United States Patent
Tokhtuev et al.

(10) Patent No.: US 8,236,573 B2
(45) Date of Patent: Aug. 7, 2012

(54) MICROFLOW ANALYTICAL SYSTEM

(75) Inventors: Eugene Tokhtuev, Duluth, MN (US); Christopher Owen, Duluth, MN (US); Anna Pilipchenko, Duluth, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 13/194,477

(22) Filed: Jul. 29, 2011

(65) Prior Publication Data

US 2011/0291033 A1    Dec. 1, 2011

Related U.S. Application Data

(63) Continuation of application No. 12/474,474, filed on May 29, 2009, now Pat. No. 8,017,409.

(51) Int. Cl.
- *G01N 21/85* (2006.01)
- *G01N 1/00* (2006.01)
- *G01N 21/00* (2006.01)

(52) U.S. Cl. ........ 436/180; 436/174; 250/576; 250/573; 250/216; 73/863.02; 73/863.01; 73/863

(58) Field of Classification Search .......... 436/180, 436/174; 250/576, 573, 216; 73/863.02, 73/863.01, 863

See application file for complete search history.

(56) References Cited

U.S. PATENT DOCUMENTS

| | | |
|---|---|---|
| 3,955,901 A | 5/1976 | Hamilton |
| 3,963,380 A | 6/1976 | Thomas, Jr. et al. |
| 4,332,534 A | 6/1982 | Becker |
| 4,344,743 A | 8/1982 | Bessman et al. |
| 4,881,876 A | 11/1989 | Laziou |
| 5,088,901 A | 2/1992 | Brauer |
| 5,261,798 A | 11/1993 | Budde |
| 5,281,107 A | 1/1994 | De Koning |
| 5,362,213 A | 11/1994 | Komatsu et al. |
| 5,376,252 A * | 12/1994 | Ekstrom et al. ............. 204/603 |
| 5,499,909 A | 3/1996 | Yamada et al. |
| 5,520,522 A | 5/1996 | Rathore et al. |
| 5,533,886 A | 7/1996 | von Der Heyde et al. |
| 5,607,565 A | 3/1997 | Azarnia et al. |
| 5,664,938 A | 9/1997 | Yang |

(Continued)

OTHER PUBLICATIONS

Grover, et al. "Practical Valves and Pumps for Large-Scale Integration Into Microfluidic Analysis Devices", Micro Total Analysis Systems Nov. 3-7, 2002, Hara, Japan, vol. 1, Dordrecht, The Netherlands: Kluwer Academic Publishers, 136-138.

(Continued)

*Primary Examiner* — Christine T Mui

(74) *Attorney, Agent, or Firm* — Fredrikson & Byron, PA

(57) ABSTRACT

A microflow analytical system includes a laminate pump assembly connectable with one or more sources of fluid, one or more pneumatic control pumps, a mixer, and a sensor. The laminate pump assembly is adapted to deliver predetermined volumes of the fluid(s) through a plurality of flow paths which are formed within layers of the assembly. Each flow path can include an inlet valve, a pump valve, and an outlet valve each of which are controllable by the pneumatic control pumps. A series of manifolds can be formed within the layers of the pump assembly to provide for simultaneous activation of selected flow paths. Delivered fluid volumes can be mixed in the mixer which, in some embodiments, may be integral with the laminate pump assembly. The sensor can measure one or more characteristics of the mixed fluids to determine one or more properties of the fluids.

20 Claims, 21 Drawing Sheets

U.S. PATENT DOCUMENTS

| | | | |
|---|---|---|---|
| 5,876,190 | A | 3/1999 | Spring |
| 5,908,603 | A | 6/1999 | Tsai et al. |
| 6,279,785 | B1 | 8/2001 | Bonningue |
| 6,283,730 | B1 | 9/2001 | Sasaki et al. |
| 6,344,722 | B1 | 2/2002 | Abel |
| 6,382,934 | B2 | 5/2002 | Budde |
| 6,390,791 | B1 | 5/2002 | Maillefer et al. |
| 6,435,840 | B1 | 8/2002 | Sharma et al. |
| 6,460,974 | B1 | 10/2002 | Lebron |
| 6,520,477 | B2 | 2/2003 | Trimmer |
| 6,531,417 | B2 | 3/2003 | Choi et al. |
| 6,589,198 | B1 | 7/2003 | Soltanpour et al. |
| 6,610,030 | B1 | 8/2003 | Baxter |
| 6,666,658 | B2 | 12/2003 | Takeuchi et al. |
| 6,716,002 | B2 | 4/2004 | Hagashino |
| 6,729,306 | B2 | 5/2004 | Koegler, III et al. |
| 6,749,407 | B2 | 6/2004 | Xie et al. |
| 6,776,591 | B1 | 8/2004 | Rinninger et al. |
| 6,796,215 | B1 | 9/2004 | Hauser et al. |
| 6,811,385 | B2 | 11/2004 | Blakley |
| 6,934,435 | B2 | 8/2005 | Kane |
| 6,948,918 | B2 | 9/2005 | Hansen |
| 6,978,913 | B2 | 12/2005 | Rousselet et al. |
| 7,000,455 | B2 | 2/2006 | Stritzelberger |
| 7,029,249 | B2 | 4/2006 | Bougamont et al. |
| 7,124,775 | B2 | 10/2006 | Chang |
| 7,156,487 | B2 | 1/2007 | Chou et al. |
| 7,195,465 | B2 | 3/2007 | Kane et al. |
| 7,284,966 | B2 | 10/2007 | Xu et al. |
| 7,309,467 | B2 | 12/2007 | Chen et al. |
| 7,328,981 | B2 | 2/2008 | Kuroda |
| 7,374,628 | B2 | 5/2008 | Takeuchi et al. |
| 2005/0037471 | A1 | 2/2005 | Liu et al. |
| 2006/0228812 | A1 | 10/2006 | Higashino et al. |
| 2006/0239862 | A1 | 10/2006 | Nakajima et al. |
| 2007/0047388 | A1 | 3/2007 | Denatale et al. |
| 2008/0063543 | A1 * | 3/2008 | Xu et al. ............ 417/395 |

OTHER PUBLICATIONS

PCT/IB2010/052378, International Search Report and Written Opinion dated Jan. 28, 2011, 6 pages.

* cited by examiner

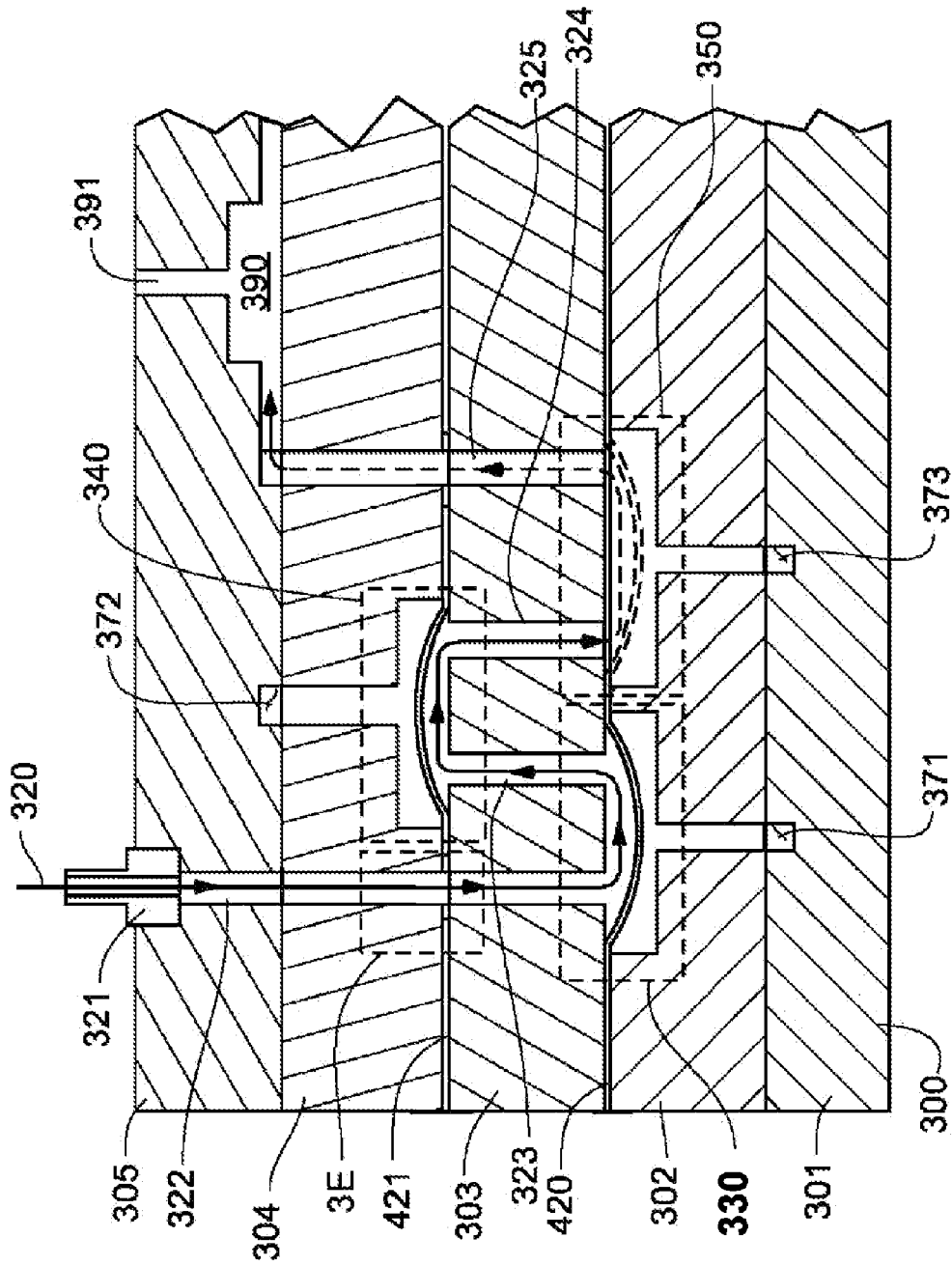

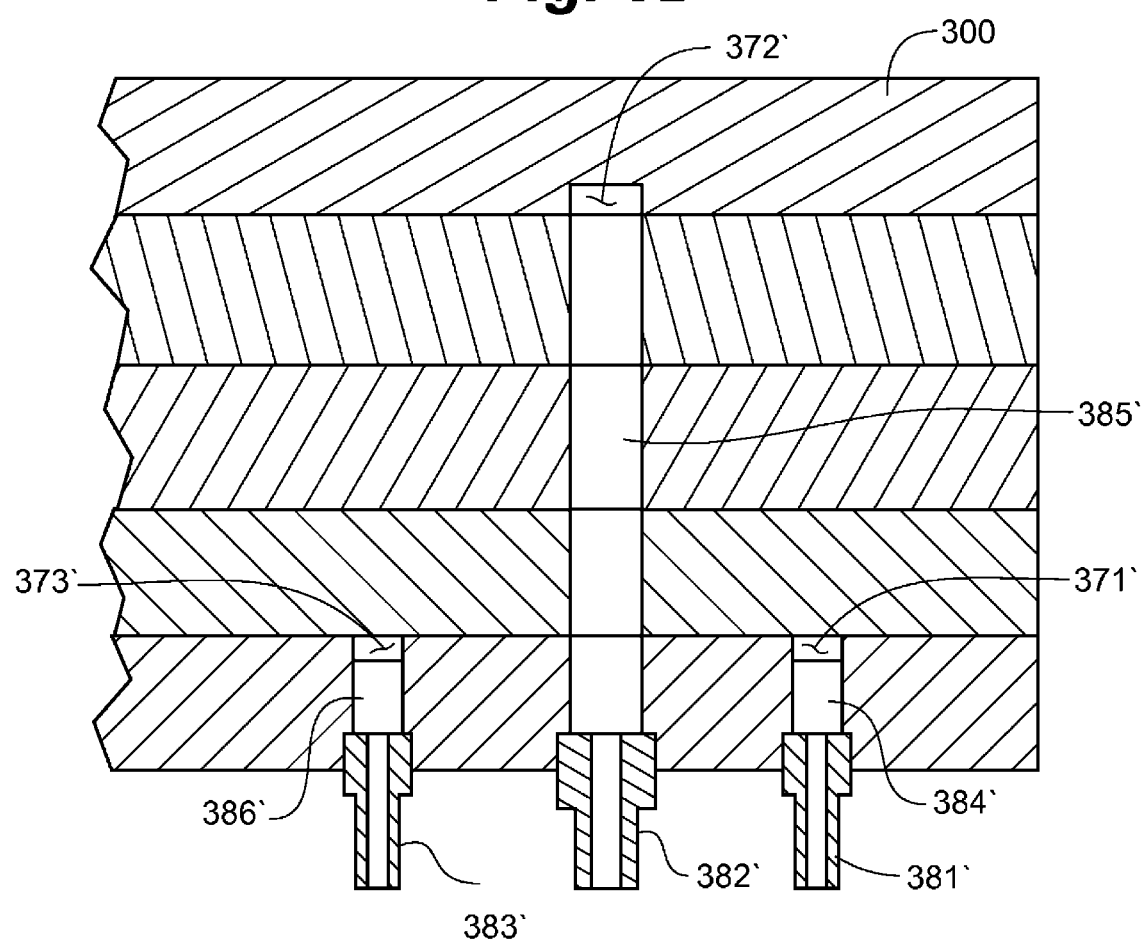

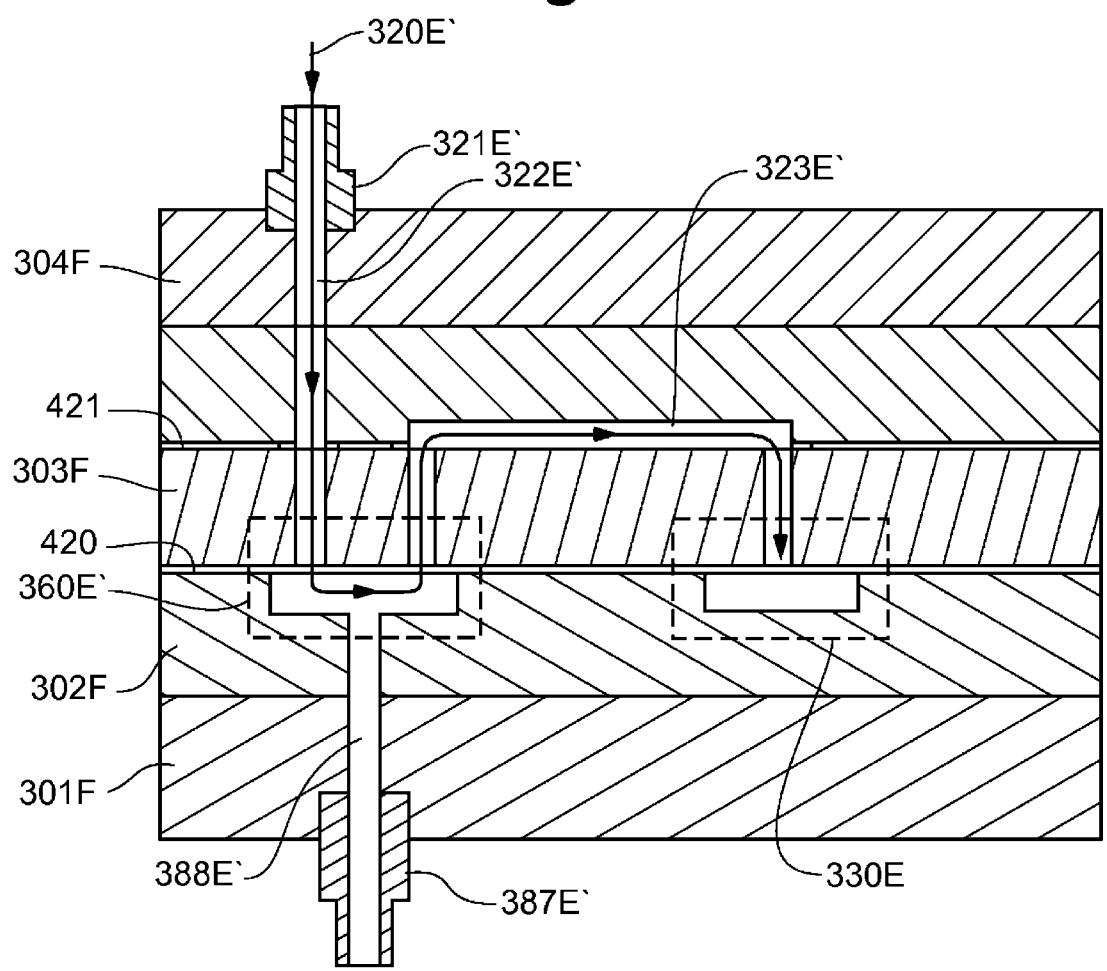

MICROFLOW ANALYTICAL SYSTEM

CROSS REFERENCE TO RELATED APPLICATION

This application is a continuation of U.S. Patent application Ser. No. 12/474,474, filed May 29, 2009, the entire contents of which are incorporated herein by reference.

FIELD

This disclosure generally relates to a microflow analytical system for performing automated chemical analysis. In particular, this disclosure relates to a microflow analytical system for determining the concentration of a peracid and peroxide within a use composition.

BACKGROUND

An analytical procedure in chemistry consists of a series of operations carried out in fixed sequence which may be considered steps or stages. One step in chemical analytical procedure often involves the delivery of predetermined volumes of one or more fluid chemicals. When performed by hand, analytical chemistry procedures can produce varied results due to a number of factors such as, for example, the usage of an improper or inaccurate volume of a fluid chemical. Moreover, manual analytical chemistry procedures can be tedious and time consuming. Accordingly, there is a desire to automate analytical chemistry procedures.

One application of analytical chemistry is to determine the concentration of one or more analytes within a composition. For example, the analytical chemical procedures can be useful in the analysis and monitoring of antimicrobial compositions. Antimicrobial compositions are used in a variety of automated processing and cleaning applications to reduce microbial or viral populations on hard or soft surfaces or in a body or stream of water. For example, antimicrobial compositions are used in various applications including kitchens, bathrooms, factories, hospitals and dental offices. Antimicrobial compositions are also useful in the cleaning or sanitizing of containers, processing facilities or equipment in the food service or food processing industries, such as cold or hot aseptic packaging. Antimicrobial compositions are also used in many other applications including but not limited to clean-in-place systems (CIP), clean-out-of-place systems (COP), washer-decontaminators, sterilizers, textile laundry machines, filtration systems, etc.

Whatever the application, an antimicrobial or "use" composition is a composition containing a defined minimum concentration of one or more active components which exhibit desired antimicrobial properties. One such category of active antimicrobial component are peracids, such as peroxycarboxylic acid (peracid), peroxyacid, peroxyacetic acid, peracetic acid, peroctanoic acid, peroxyoctanoic acid and others.

The concentration of active components in the use composition is chosen to achieve the requisite level of antimicrobial activity. In use compositions in which one or more peracids are the active component, and in the instance of a recirculating process, the concentration of hydrogen peroxide tends to increase over time while the concentration of peracid decreases. However, in order to maintain the requisite level of antimicrobial activity, the amount of peracid in the use composition must be maintained at a defined minimum concentration. In addition, as the amount of hydrogen peroxide in the use composition increases, the use composition may exceed a defined maximum concentration of hydrogen peroxide in the solution. In some applications, for example bottling line cleansing, the allowable amount of residual hydrogen peroxide is subject to government regulations. Once the hydrogen peroxide concentration exceeds the maximum concentration, the spent use composition is discarded and a new use composition generated.

To ensure that the amount of peracid is maintained at or above some minimum concentration and to determine when the amount of hydrogen peroxide reaches or exceeds a maximum concentration, it is necessary to determine the concentration of peracid(s) and hydrogen peroxide in the use composition. In the past, to determine both the peracid concentration and the hydrogen peroxide concentration in a use composition has required multiple time consuming manual titrations, several different reagents and relatively large volumes of use composition. Moreover, past devices and methods for determining both peracid and hydrogen peroxide concentrations were effective over only a narrow range of concentrations.

SUMMARY

In a first aspect, a microflow analytical system is disclosed. Embodiments of the microflow analytical system include a laminate pump assembly adapted to control parallel delivery of a plurality of fluids, a pneumatic control pump for controlling the delivery of fluids through the laminate pump assembly, a mixer for mixing the delivered fluids, and a sensor configured to obtain response data indicative of a characteristic of the mixed fluids. The laminate pump assembly can include a plurality of flow paths formed therewithin. Each flow path of the laminate pump assembly includes a pump valve, an inlet valve, and an outlet valve. The inlet valve can be connected to selectively provide fluid communication between an inlet connector and the pump valve. The outlet valve can be connected to selectively provide fluid communication between the pump valve and an outlet channel. Each of the pump valve, inlet valve, and outlet valve can comprise a chamber formed at an interface of two layers of the laminate pump assembly. A pneumatically actuated membrane divides the chamber into a fluid flow cavity and a pneumatic control cavity such that the delivery or removal of a pneumatic fluid to the pneumatic control cavity can be used to control the valves. For example, delivery of a pneumatic fluid to the pneumatic control cavity can cause the fluid flow cavity to collapse, thereby blocking the flow path and forcing fluid within the fluid flow cavity out along the flow path. Removal of pneumatic fluid from the pneumatic control cavity can likewise cause the fluid flow cavity to open, thereby drawing fluid within the flow path into the fluid flow cavity and permitting fluid flow through the flow path.

In another aspect, a method for measuring a concentration of one or more analytes within a use composition is disclosed. The method can include providing a laminate pump assembly adapted to control the delivery of volumes of a plurality of fluids, a mixer, and a sensor. The laminate pump assembly can include a plurality of flow paths formed therewithin, each flow path comprising a plurality of microfluidic valves adapted to deliver a metered fluid flow from an inlet connector of the flow path to an outlet channel of the flow path. The mixer can be connected in fluid communication with the outlet channels of the laminate pump assembly and adapted to mix fluid delivered from two or more of the flow paths. The sensor can be coupled with the mixer and configured to obtain response data indicative of a reaction of the mixed fluids. The method further includes connecting a source of the use composition and a source of at least one reagent with the inlet connectors. The laminate pump assembly can then be activated, thereby causing metered volumes of use composition and reagent to be delivered to the mixer. The metered volumes of use composition and reagent can then be mixed. The method further includes obtaining response data from the sensor indicative of the concentration of the one or more analytes within the use composition. The concentration of the one or more analytes can then be calculated based on the response data.

BRIEF DESCRIPTION OF THE DRAWINGS

The following drawings are illustrative of particular embodiments of the invention and therefore do not limit the scope of the invention. The drawings are not to scale (unless so stated) and are intended for use in conjunction with the explanations in the following detailed description. Embodiments of the invention will hereinafter be described in conjunction with the appended drawings, wherein like numerals denote like elements.

FIG. 3C is a cross-sectional view of a flow path of the laminate pump assembly of FIG. 3A taken along line C-C.

FIG. 3D is a cross-sectional view of the laminate pump assembly of FIG. 3A taken along line D-D.

FIG. 3G is a cross-sectional view of the laminate pump assembly of FIG. 3F taken along line G-G.

DETAILED DESCRIPTION OF ILLUSTRATIVE EMBODIMENTS

Figure 1:
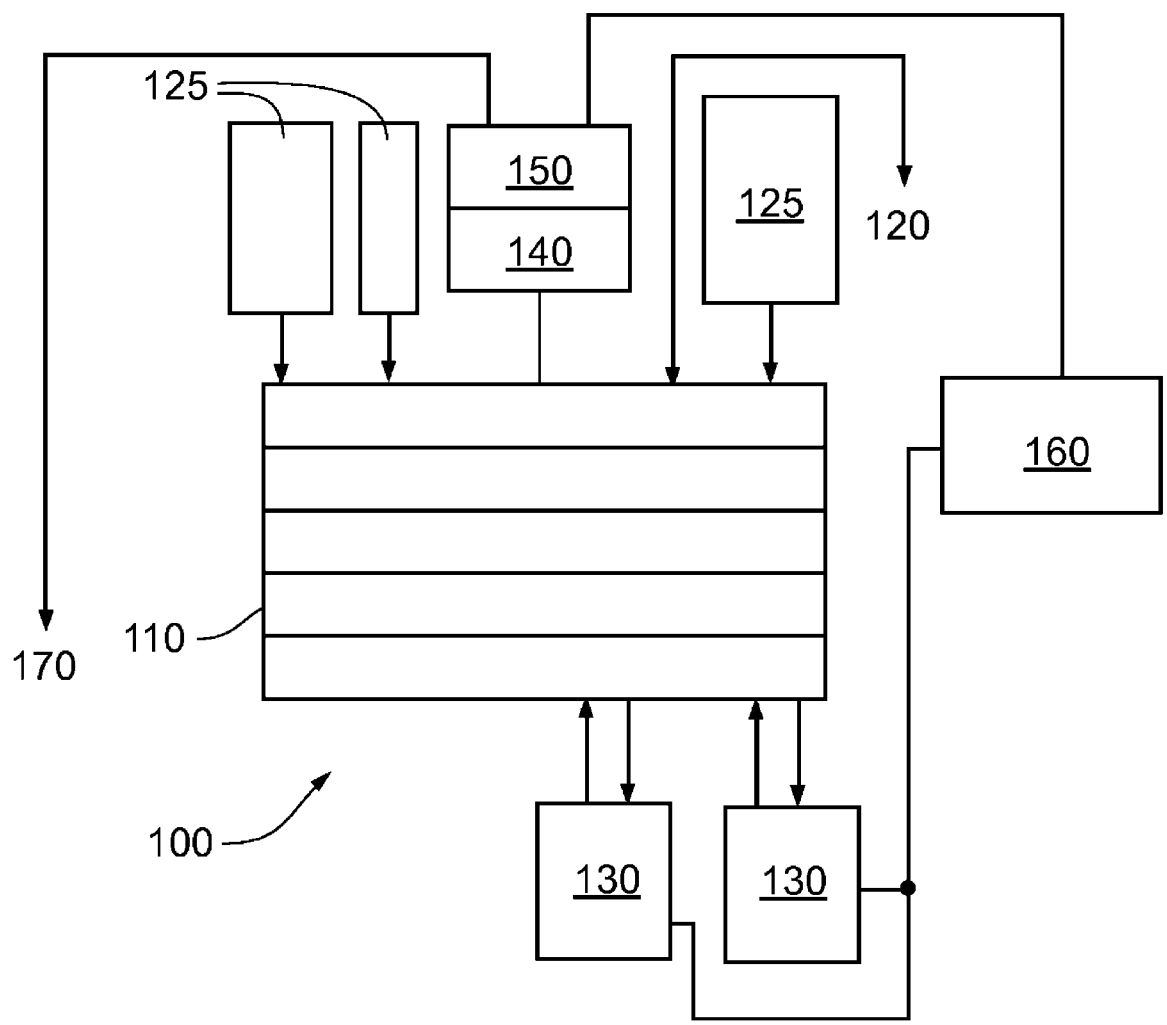
FIG. 1 is a schematic of a microflow analytical system according to some embodiments.

FIG. 1 shows a schematic of a microflow analytical system 100 according to some embodiments. The system 100 includes a laminate pump assembly 110 comprising a plurality of layers that define actuatable flow paths. The laminate pump assembly 110 is adapted to control the parallel delivery of a plurality of fluids from fluid sources (e.g. use composition input 120, and/or fluid reservoirs 125) to analytical instrumentation. One or more pneumatic control pumps 130 can be coupled with the laminate pump assembly 100 to selectively actuate microflow valves formed therewithin, and thereby control the flow of fluid through the laminate pump assembly 100. In some embodiments, the analytical instrumentation comprises a mixer 140 and a sensor 150. In such systems, the sensor 150 can obtain response data indicative of characteristics of the mixed fluids. This response data can then be processed by a processor 160 to determine characteristics of properties of one or more of the fluids.

Microflow analytical systems, according to some embodiments, enable the automation of manual wet chemical analytical procedures. For example, the microflow analytical system 100 can be configured as a use composition monitor. A use composition monitor may be connected to a source of use composition 120, to monitor characteristics of the use composition such as, for example, the content or concentration of selected analytes. In particular, some embodiments are well suited for use as a use composition monitor for determining the concentration of peracid and/or hydrogen peroxide in a use composition. For example, the use composition may be monitored to ensure that the concentration of peracid satisfies at least a minimum threshold concentration. The use composition may also be monitored to determine when the concentration of hydrogen peroxide exceeds a maximum threshold concentration. Of course, embodiments of the microflow analytical systems disclosed herein should not be limited to monitoring devices, for example, such systems can be used as analytical instruments or for other purposes.

In the embodiment shown in FIG. 1, the microflow analytical system 100 includes a laminate pump assembly 110 under control of a controller 160. The laminate pump assembly 110 controls the parallel delivery of fluids from connected fluid sources 120, 125 to a fluid outlet channel via fluid flow paths formed within the assembly 110. Control of the fluid flow paths can be implemented by pneumatically controlled valves formed at the interface of layers of the laminate pump assembly 100. Accordingly, some embodiments include one or more pneumatic control pumps 130 which actuate the valves within the laminate pump assembly 110.

Figure 2:
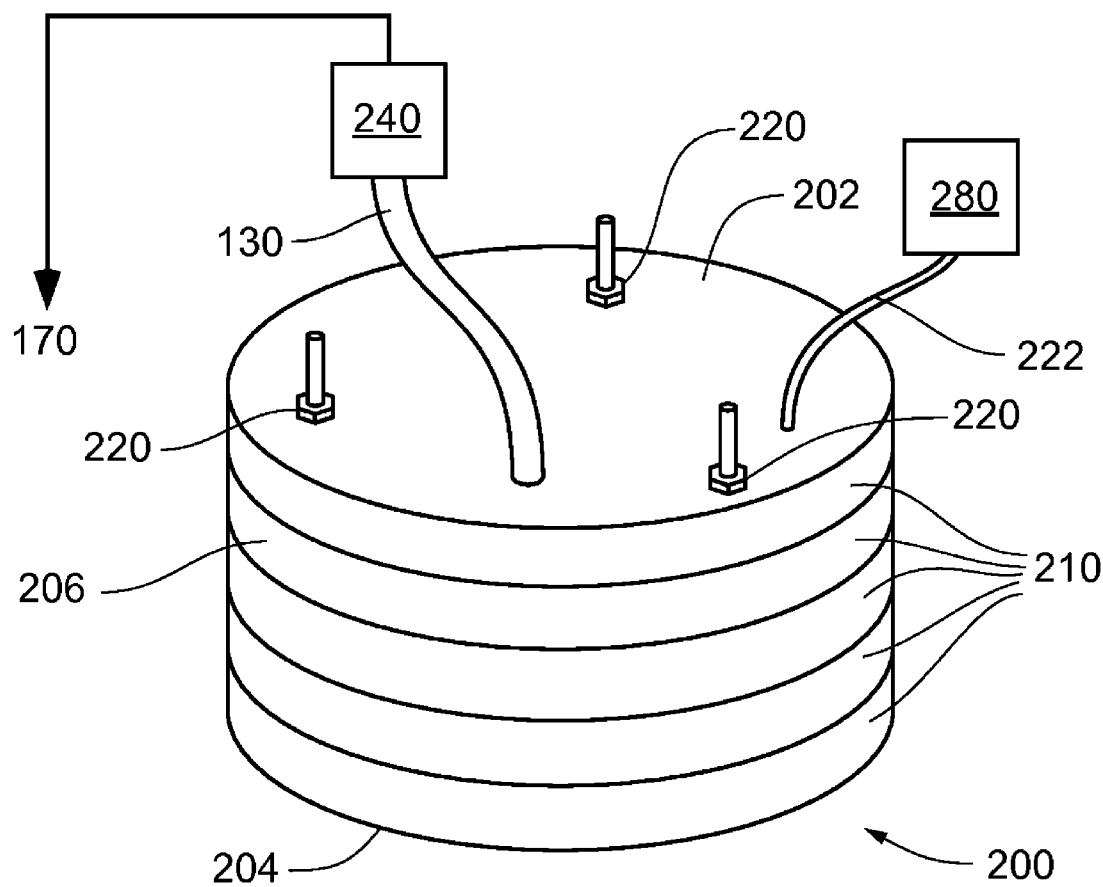
FIG. 2 is a schematic view of an implementation of a laminate pump assembly according to some embodiments.

FIG. 2 shows an implementation of a laminate pump assembly 200 according to some embodiments. The laminate pump assembly 200 comprises a plurality of layers 210 comprising a substantially rigid material. Some of the layers 210 can be separated by one or more thin membranes. The layers and membranes can be joined together in a compression fit such that channels formed therewithin are sealed. In some embodiments, snapping mechanisms or mechanical fasteners can be used to compress and combine sequential layers. Alternatively, the layers can be clamped or fused together. The layer material should be selected from materials having high resistivity to water and chemicals used for specific embodiment. For example, in some embodiments, the layers comprise a molded plastic. In some embodiments, the layers comprise a fluoropolymer, such as PVDF (KYNAR®), FPM, PTFE (Teflon®) or others. Layers or portions of layers which have no direct contact with water and/or chemicals can be made of other materials such as acetal, PVC, or ABS (acrylonitrile-butadienestyrene).

In the embodiment of FIG. 2, the assembly 200 is generally cylindrical having a top surface 202, a bottom surface 204, and lateral surface 206. Inlet connectors 220, 222 are shown on the top surface of the assembly 200. The inlet connectors 220, 222 provide for the connection of fluid sources (e.g. a source of use composition 280) to flow paths formed within the assembly 200. The layers 210 include patterns of channels, bores, chambers, and other features formed on interior surfaces of the layers 210. When the layers are aligned and joined together, these features define the flow paths. The flow paths connect the fluid inlet connectors 220, 222 to one or more outlet channels. Here, the outlet channels 230 are provided on the top surface 202 of the assembly 200 and are connected with analytical instrumentation 240 adapted to analyze the fluids.

Figure 3A:
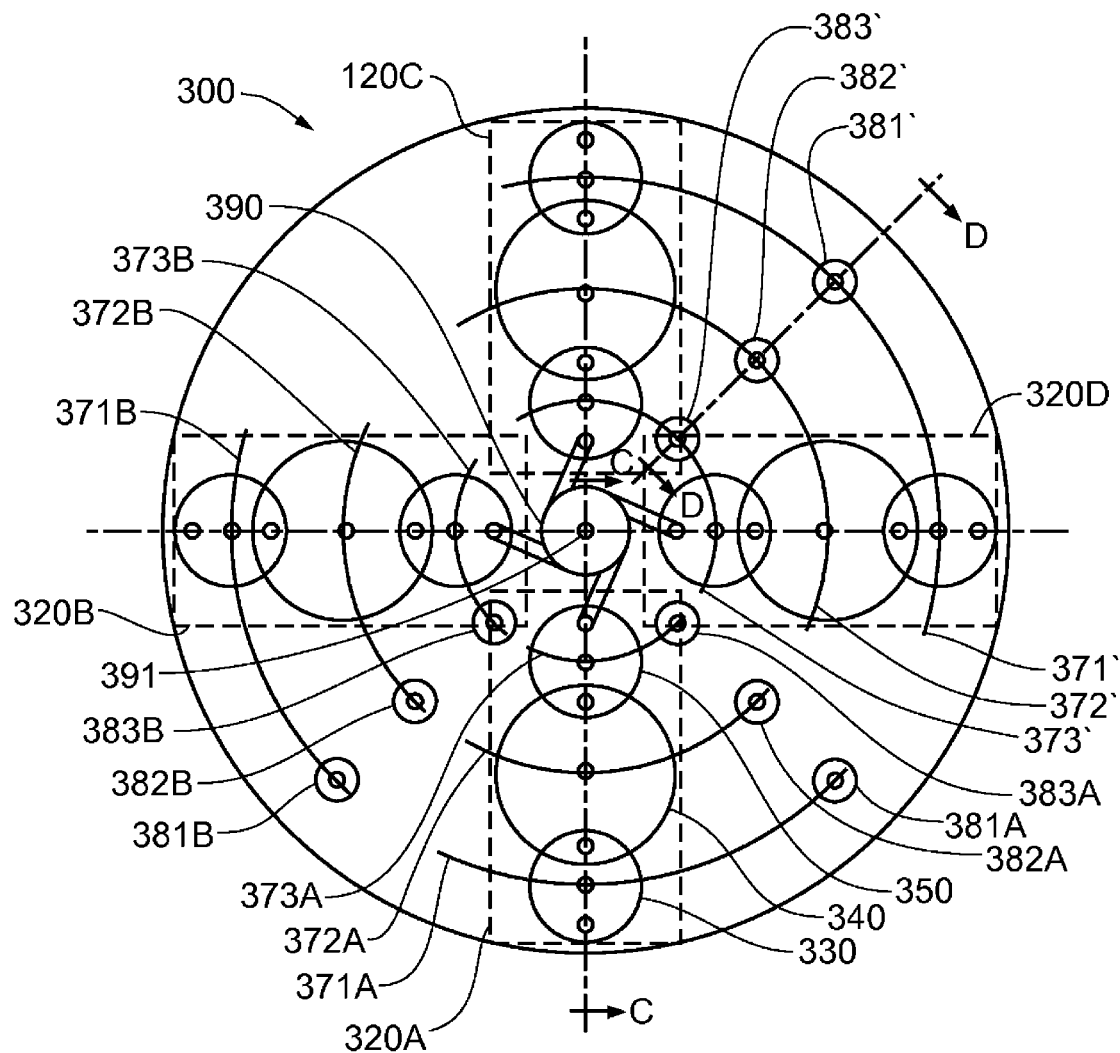
FIG. 3A is a partially transparent, top plan view of a laminate pump assembly according to some embodiments.

The formation and operation of the fluid flow paths will now be discussed with reference to FIGS. 3A-3D. FIG. 3A shows a semi-transparent, top plan view of a laminate pump assembly 300 according to some embodiments indicating internal features of the assembly 300. The assembly 300 includes four flow paths 320 radially disposed within the five layers 301, 302, 303, 304, 305 of the assembly 300. For purposes of identifying a specific one of the flow paths 320, a letter A-D will be appended to the referenced part number. Part number references not including an appended letter should be construed to apply to any or all of the identified parts. Each flow path 320 comprises an inlet valve 330, a pump valve 340, and an outlet valve 350. Each valve is connected to a control manifold 371, 372, 373 which provides for connection to pneumatic control pumps at pneumatic connection interfaces 381, 382, 383.

Figure 3B:
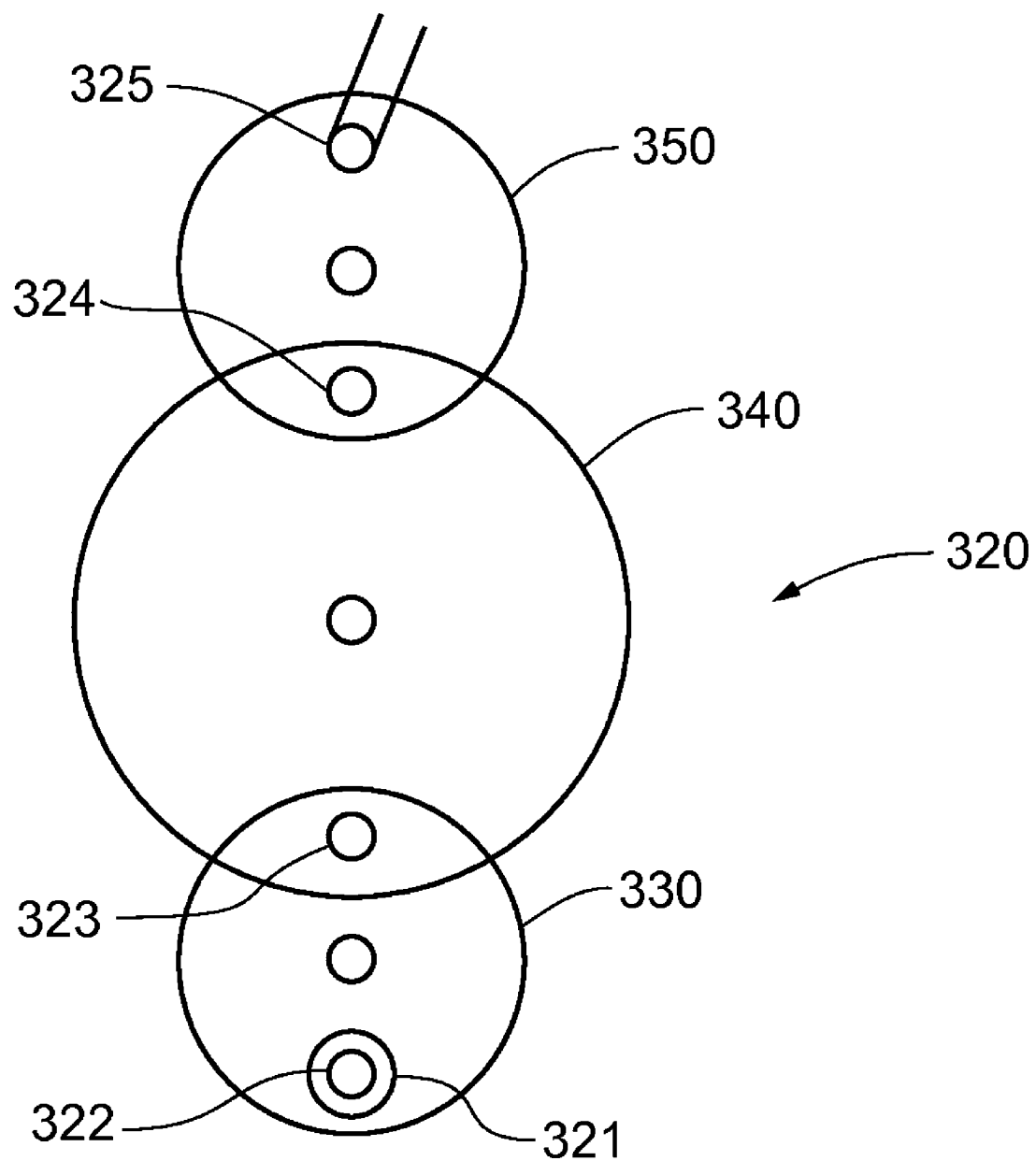
FIG. 3B is a top plan view a flow path of the laminate pump assembly of FIG. 3A according to some embodiments.

FIGS. 3B and 3C, respectively, show a top plan view and cross-sectional view along line C-C of a flow path 320 of the laminate pump assembly 300 of FIG. 3A. The flow path 320 begins at inlet connector 321 which provides for connection of the fluid source to the flow path 320. Passage 322 delivers fluid from the inlet connector 321 to inlet valve 330. Operation of the inlet and other valves of the flow path, will be discussed below. When opened, the inlet valve 330, allows fluid to flow to pump valve 340 via passage 323. From the pump valve 340, fluid flows to the outlet valve 350 via passage 324. And from the outlet valve 350, fluid flows to outlet channel 325. In this embodiment, the assembly 300 includes an integral mixer 390, which connects with the outlet channels 325 of each of the flow paths.

FIG. 3D shows a cross-sectional view of the laminate pump assembly 300 taken along line D-D of FIG. 3A. This view shows the passages 384', 385', 386' which connect control manifolds 371', 372', 373' with pneumatic control pump connectors 381', 382', 383'. In operation, pneumatic control pump connectors 381', 382', 383' are connected to pneumatic control pumps which pressurize or depressurize pneumatic control chambers of each valve, thus controlling fluid flow within the flow paths. As can be seen in FIG. 3A, the use of control manifolds allows valves of multiple flow paths to share a common pneumatic control pump. For example, each of the valves of flow paths 320A and 320B have individual control manifolds (e.g. the valves of flow path 320A have control manifolds 371A, 372A, 373A, and the valves of flow path 320B, have control manifolds 371B, 372B, 373B). Accordingly, these flow paths are individually actuatable. Each of the valves of flow paths 320C and 320D, however, share control manifolds 371', 372', 373'. Accordingly, flow paths 320A and 320B are individually actuatable separate from flow paths 320C and 320D which are simultaneously actuatable.

Figure 4A:
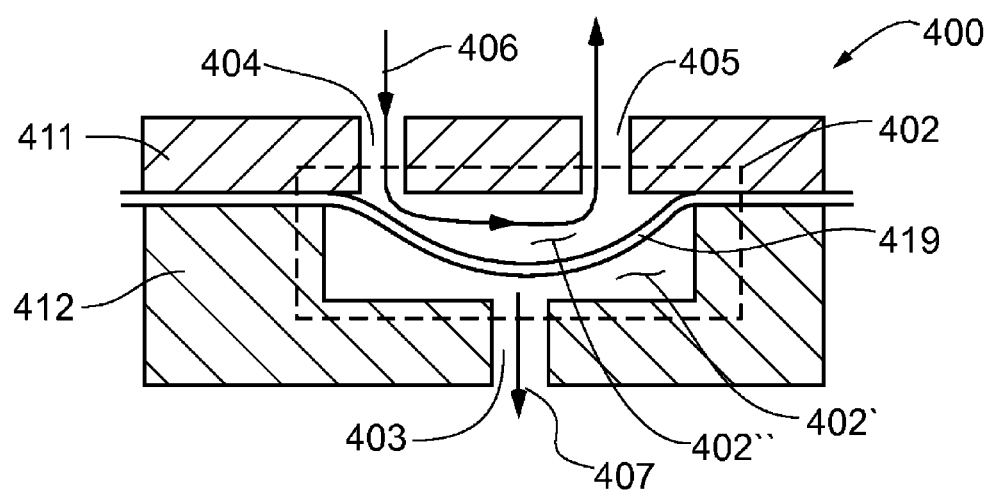
FIG. 4A is a cross-sectional view of an "open" pneumatically actuated diaphragm valve according to some embodiments.
Figure 4B:
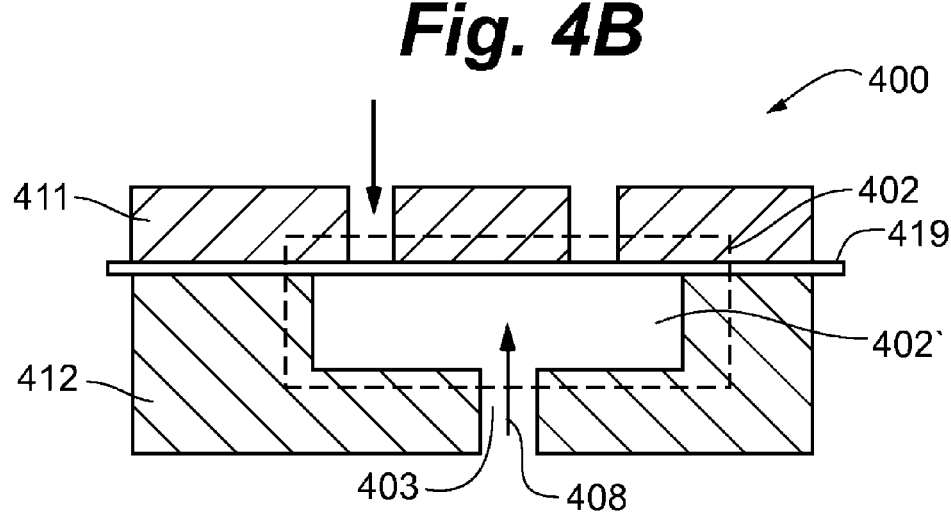
FIG. 4B is a cross-sectional view of a "closed" pneumatically actuated diaphragm valve according to some embodiments.

Each of the valves 330, 340, 350 of the flow path 320 can comprise a pneumatically actuated diaphragm valve such as that shown in FIGS. 4A and 4B. A pneumatically actuated diaphragm valve 400 comprises a chamber 402 formed at an interface of two layers 411, 412 of the laminate pump assembly. A membrane 419 comprising a flexible, expandable material divides the chamber 401 into a pneumatic control chamber 402' and a fluid flow chamber 402". The pneumatic control chamber 402' includes a connection to a pneumatic control passage 403 which connects the pneumatic control chamber 402' with a pneumatic control pump (e.g. via a control manifold). The fluid flow chamber 402" is in fluid communication with a fluid inlet passage 404 and a fluid outlet passage 405. When pressure within the pneumatic control chamber 402' is low the fluid flow chamber 402" is "opened" allowing for fluid to flow along the fluid path 406 from fluid inlet passage 404 to fluid outlet passage 405. This can occur, for example, by removing pneumatic fluid (for example, air) from the control chamber 402', e.g. according to arrow 407. When pressure within the pneumatic control chamber is increased the fluid flow chamber 402" collapses, thereby preventing the flow of fluid from the fluid inlet passage 404 to the fluid outlet passage 405 and forcing any fluid within the fluid flow chamber 402" out one of the passages 404, 405. In this state, the valve 400 is said to be "closed." The valve 400 can be closed, for example, by delivering pneumatic fluid to the control chamber 402', e.g. according to arrow 408.

In some embodiments, the chamber 402 is formed at a recessed area within a single surface layer 412. Forming the chamber 402 in this manner can reduce fabrication demands by requiring fewer and more easily performed manufacturing techniques to be employed. Of course, the chamber can be implemented by providing and aligning recesses in adjacent layers 411, 412. Moreover, while the chambers of valves 330, 340, 350 in the embodiment of FIG. 3A are circular, the device should not be limited to such. For example, chambers can be square, rectangular, or otherwise shaped. In addition, generally any acceptable method can be used to fabricate the chambers disclosed herein. For example, in some embodiments, each layer comprises molded plastic having the chambers, passages, channels, and other features molded into the part during fabrication. Alternatively, channels and chambers can be etched and passages can be drilled into layers once the layers have been formed.

Pneumatically actuated valves 400 further comprise a pneumatically actuated membrane 419 comprising a flexible film layer. In addition to being flexible, the membrane 419 should be resilient to fluids which the system will accommodate. Moreover, the membrane 419 should be impermeable to fluids, so as to provide fluid separation between the pneumatic control chamber 402' and the fluid flow chamber 402". For example, in some embodiments the membrane 419 comprises a synthetic fluoropolymer film such as PTFE (polytetrafluoroethylene or polytetrafluoroethene), e.g. Teflon. In addition, it is preferable that the membrane comprises a material and is installed such when the pneumatic control pumps are turned off, there is enough tension in the membrane to maintain the valves in a closed state. This can prevent unwanted fluid flow and leakage.

Figure 3E:
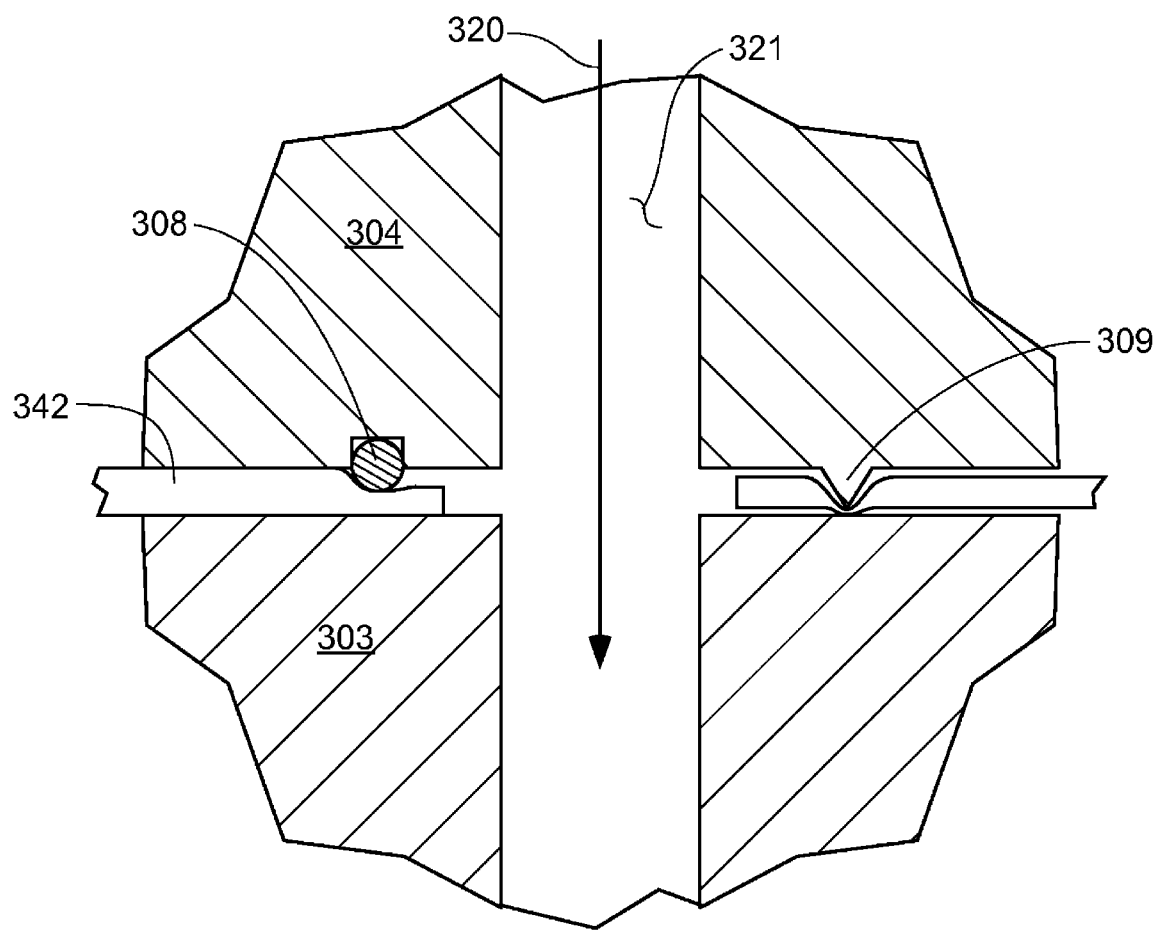
FIG. 3E is an enlarged sectional view of region 3E identified in FIG. 3C.

The membrane 419 is positioned within the valves 400 so as to completely separate the pneumatic control chamber 402' and the fluid flow chamber 402". The membrane 400 can be sized slightly larger in diameter than the chamber 402 which it divides and be clamped in place by the adjacent joined layers 411, 412 of the assembly. Alternatively in some embodiments, such as that shown in FIG. 3C, the membrane comprises a membrane layer 420, 421 that covers substantially the entire surface of the layer. In such embodiments, a single membrane layer e.g. membrane layer 420, may serve as the membrane for multiple valves, i.e. inlet valve 330 and outlet valve 350. At each valve, the fused layers about the membrane provide a clamping force at the borders of each chamber, thus securing the membrane in place. As needed, a membrane layer may include features to allow for passages. For example, FIG. 3E shows an enlarged view of region 3E identified in FIG. 3C. At this region, passage 321 crosses the interface of layers 303, 304 that sandwich the membrane layer 421. To accommodate passage 321, the membrane layer 421 includes a hole. In addition, some embodiments may include features such as an o-ring 308 or layer protrusion 309 that prevent leakage of fluid from the flow path at this junction. Moreover, such leakage prevention features may be provided about valve chambers or other features to prevent leakage of fluid between layers.

Figure 5:
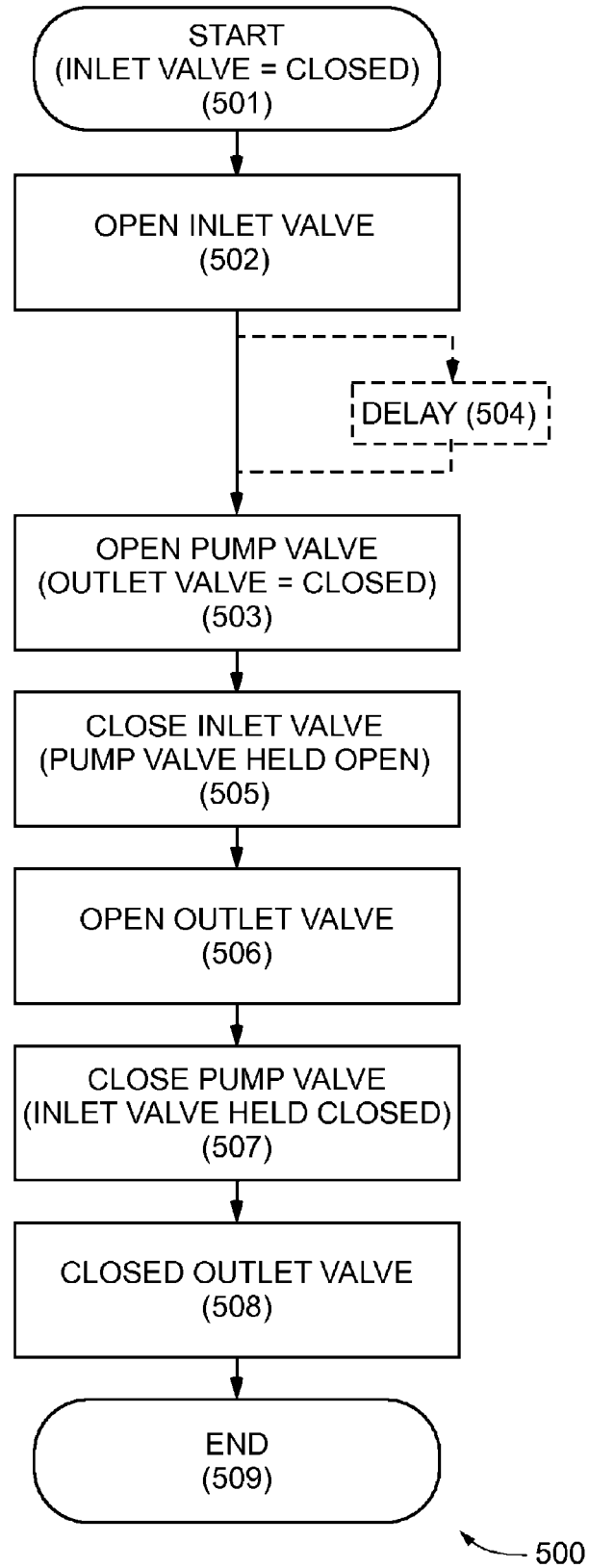
FIG. 5 is a flow chart illustrating a pump cycle activation sequence according to some embodiments.

With reference to FIG. 3C, an activation sequence of the valves 330, 340, 350 of the flow path 320 will now be described. The activation sequence shown in FIG. 5 and described below provides for the sequential intake (aspiration) and expelling (dispensing) of fluid from each of the valves resulting in the delivery of a predetermined, metered volume of fluid from a connected fluid source to the outlet channel 325. Such activation sequence may be referred to as a "pump cycle" 500.

In an initial state (501), the inlet valve 330 is closed, preventing fluid flow along the flow path 320. To begin the pump cycle, the inlet valve 330 is opened (502). This draws fluid from the connected fluid source in through passage 322 via inlet connector 321. Pump valve 340 is then opened, while outlet valve 350 remains closed (503). The opening of the pump valve 340 can occur simultaneously with the opening of the inlet valve 330, or following an optional delay (504). Pump valve 340 can then be held open as inlet valve 330 is closed (505). At this point, a metered volume of fluid is held within the flow path 320 at the fluid flow chamber of the pump valve 340 and passages 323, 324. Outlet valve 350 can then be opened (506), connecting channel 324 with outlet channel 325. With inlet valve 330 held closed, pump valve 340 can then close (507), forcing fluid out via the fluid flow path 320 through channel 324 and the fluid flow path of the opened outlet valve 340 to the outlet channel 325. Outlet valve 340 can then be closed (508), returning the system to its original state (509).

The metered pump cycle volume of fluid dispensed via the pump cycle 500 described above depends largely on the dimension of the valves and passages. In particular, the metered volume is governed by the volume of the fluid flow chamber of the pump valve 340 and the volumes of passages 323 and 324. In some embodiments, these features are dimensioned such that the pump cycle volume is less than 100 microliters. For example, in some embodiments, pump cycle volume of each flow path is approximately 30 microliters. In such an embodiment, the inlet and outlet valves can have volumes of approximately 5 microliters each, and the pump valve can have a volume of approximately 30 microliters, for example.

Due to the small volumes being moved, and the quick action of the pneumatically actuated valves 330, 340, 350, complete pump cycles can be executed rapidly. For example, in some embodiments, a single pump cycle 500 can occur in less than 10 seconds. In some embodiments, each pump cycle 500 can take approximately 3 seconds, each valve actuating within approximately 0.5 seconds or less. Thus, each flow path can rapidly deliver predetermined volumes of fluid.

Figure 10A:
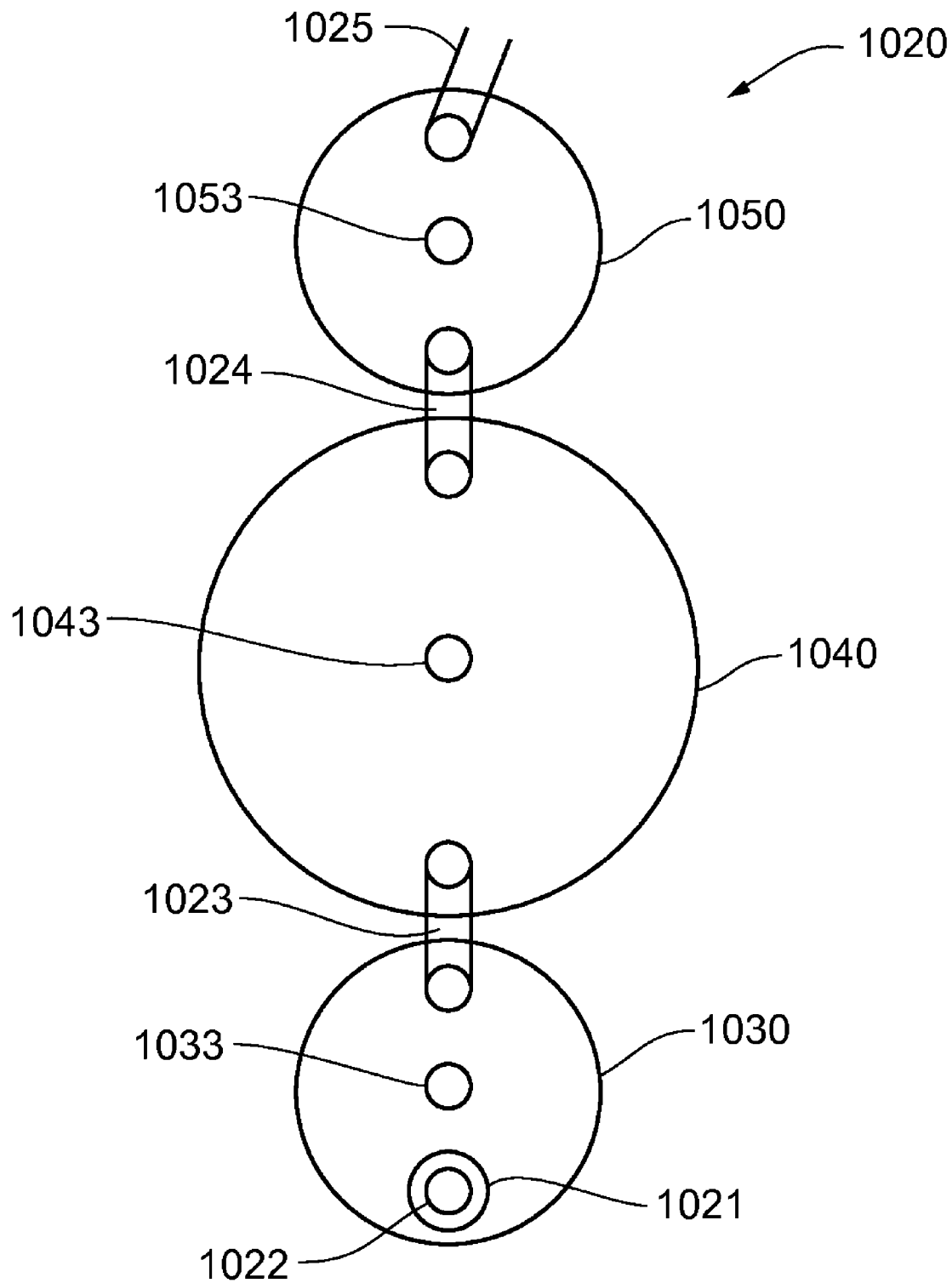
FIG. 10A is a top plan view a flow path of a laminate pump assembly according to some embodiments.
Figure 10B:
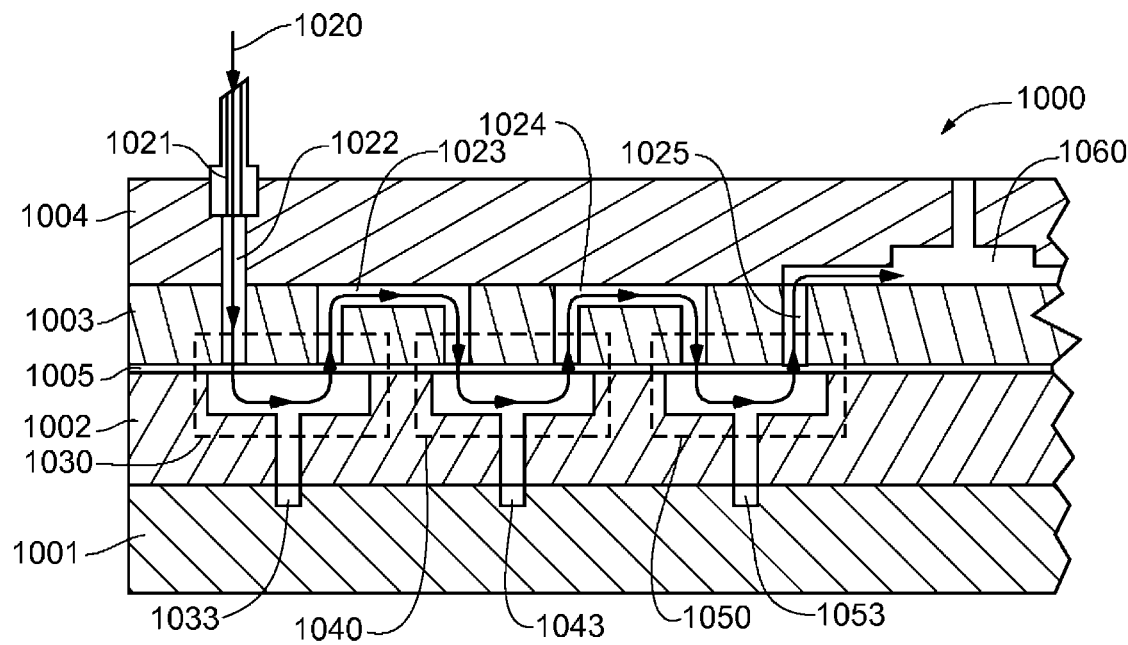
FIG. 10B is a cross-sectional view of the flow path of FIG. 10A according to some embodiments.

FIGS. 10A and 10B show views of another embodiment of a flow path 1020 according to some embodiments. FIG. 10A shows a top plan view of the flow path 1020, and FIG. 10B shows a cross-sectional view of the flow path 1020 within a laminate pump assembly 1000 comprising four rigid layers 1001, 1002, 1003, 1004 and a single membrane 1005. This flow path 1020 is similar in structure and operation to that shown in FIGS. 3B and 3C, however a horizontal valve arrangement (rather than a stacked arrangement) has been utilized. In this embodiment, each of the valves 1030, 1040, 1050 reside at a single layer interface, i.e. the interface of layer 1002 and layer 1003. Accordingly, only one membrane 1005 need be utilized. However, the horizontal valve arrangement can require a larger laminate assembly surface area in order to fit all valve chambers onto the device because it does not utilize space within the vertical dimension as does the stacked arrangement. Of course, embodiments of the invention are not be limited to the stacked and horizontal arrangements shown as one of ordinary skill in the art can appreciate different or combinations of valve arrangements that can be utilized to accomplish the purposes taught herein.

The flow path 1020 begins at inlet connector 1021 which provides for connection of the fluid source to the flow path 1020. Passage 1022 delivers fluid from the inlet connector 1021 to inlet valve 1030. Operation of the inlet and other valves of the flow path 1020, is identical to that described above. When opened, the inlet valve 1030, allows fluid to flow to pump valve 1040 via passage 1023. In contrast to the previously described embodiment, passage 1023 comprises a horizontal passage contained within layer 1003. From the pump valve 1040, fluid flows to the outlet valve 1050 via passage 1024, which is also a horizontal passage. And from the outlet valve 1050, fluid flows to outlet channel 1025. In this embodiment, the assembly 1000 includes an integral mixer 1060, which, as above, can connect with the outlet channels 1025 of each of a plurality of flow paths contained within a single laminate assembly 1000.

Control of the valves 1030, 1040, 1050 can be accomplished as described above. Each of the valves 1030, 1040, 1050 includes a pneumatic control passage 1033, 1043, 1053 connectable to one or more pneumatic control pumps. As with the devices described above, such control passages 1033, 1043, 1053 can be connected with manifolds to connect two or more flow paths. Actuation of the control paths 1020 to effectuate delivery of a volume of fluid therethrough can likewise be accomplished as described above, e.g. according to pump cycle 500.

In systems which process multiple flow paths in parallel (i.e., each parallel flow path simultaneously executes a pump cycle), for example, those including control manifolds, fluid preparation of sample mixtures can occur significantly faster than previously known systems. For example, in a peracid/peroxide concentration monitor, sample preparation of previously existing devices took on the order of 5 minutes. Now, according to some embodiments of the present invention, the sample preparation steps can be accomplished in less than 10 seconds, e.g. within 3 seconds. The improved sample preparation time afforded by embodiments according to the present invention can be especially useful in use composition monitoring applications to decrease measurement sequence times. Reduced measurement sequence times can result in a use composition monitor that can provide more timely notification of threshold events.

Figure 3F:
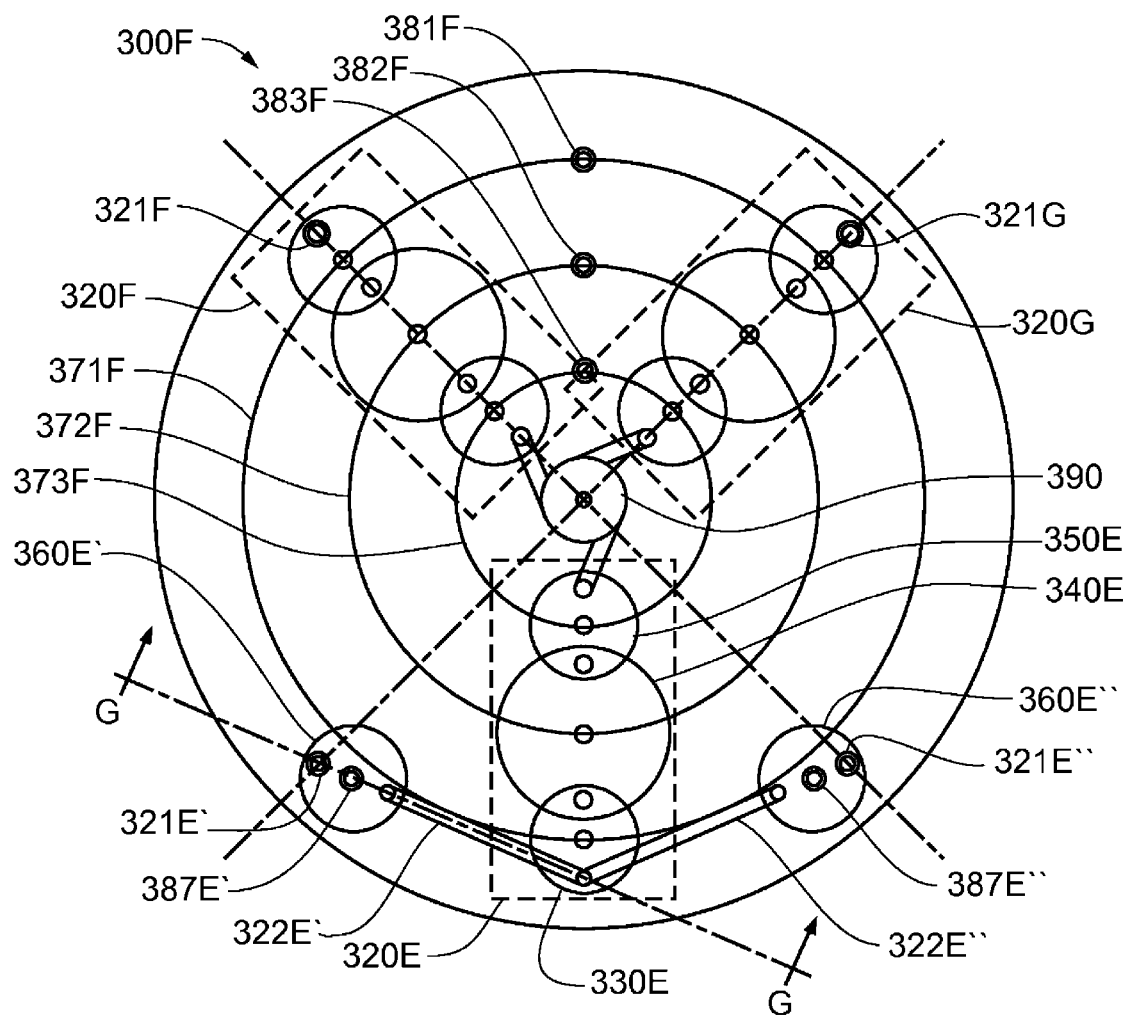
FIG. 3F is a partially transparent, top plan view of a laminate pump assembly adapted for use with a peracid and/or peroxide concentration monitor according to some embodiments.

FIGS. 3F and 3G show views of an exemplary laminate pump assembly 300F adapted for use as a sample preparation system for a peracid/peroxide concentration monitor. The laminate assembly 300F comprises three flow paths 320E, 320F, 320G adapted to deliver volumes of three fluids to an integral mixer 390. This embodiment includes two selector valves (pneumatic control valves 360E', 360E" within the laminate pump assembly 300F) connected to a single flow path 320E so that use composition or a blank (e.g. water) can be selectively introduced depending upon whether the monitor is performing a "measurement cycle" or a "reagent blank cycle." Accordingly, the inlet connectors 321E', 321E" of the selector valves 360E', 360E" can be connected with a source of use composition and a source of water, respectively. The other flow paths 320F, 320G can include connections to a source of reagent and a source of acid. For example, in some embodiments, the inlet connector 321F is connected with a source of reagent (e.g. potassium iodide) and the inlet connector 321G is connected with a source of acid (e.g. acetic acid). In the embodiment of FIG. 3F, the inlet connectors 321 have been arranged about the top of the laminate pump assembly 300F in a pattern and spacing identical to that of the embodiment shown in FIG. 3. Accordingly, such devices can utilize a cartridge system such as that described with respect to FIGS. 9A-9D below.

In this embodiment, each of the flow paths 320 are simultaneously actuatable. The laminate pump assembly 300F includes pneumatic control manifolds 371F, 372F, 373F for providing such simultaneous actuation. Each of the control manifolds are connectable to a pneumatic control pump at respective pneumatic connection interfaces 381F, 382F, 383F. As described below, in some embodiments a single pneumatic control pump can be utilized to control the actuation of valves of the flow paths 320 via connection to the pneumatic control interfaces 381F, 382F, 383F and pneumatic control manifolds 371F, 372F, 373F.

FIG. 3G is a cross-sectional view taken along line G-G of FIG. 3F which illustrates a selector valve connection 320E' to the flow path 320E. The selector valve connection 320E' operates based on the inclusion of a selector valve 360E' formed within the laminate pump assembly 300F. In this embodiment, the selector valve comprises a pneumatic control valve 360E', which can be constructed and operate according to the pneumatic control valve described with reference to FIGS. 4A and 4B. The pneumatic control valve 360E' can be formed within the layers of the laminate pump assembly, for example, at the interface of layers 302F and 303F. Of course, the pneumatic pump can be formed at other layers, provided a membrane 420 is located at such junction and so long as the selector valve placement does not interfere with the placement of other components of the laminate pump assembly 300F.

In operation, the selector valve connection 320E' operates much like the flow paths previously discussed. Fluid can enter the device at inlet connector 321E' and pass through inlet passage 322E' to the selector valve 360E'. The selector valve 360E' can be controlled by a pneumatic control pump which can be connected to the assembly at pneumatic control connection interface 387E' which is connected to the selector valve 360E' by passage 388E'. Although the embodiment shows a direct connection between the selector valve and control connection interface, some embodiments may include one or more control manifolds to connect multiple selector valves to a common pneumatic control source for simultaneous actuation. The outlet of the selector valve 360E' is connected to passage 323E' which provides connection to the inlet valve 330E of flow path 320E. Thus, when selector valve 360E' is open, a fluid connection is provided from fluid inlet connector 321E' to the flow path 320E, and no such connection is provided when the selector valve 360E' is closed.

With reference to the pneumatic control pumps described below, a single pneumatic control pump can be utilized to control the pair of selector valves 360E', 360E". For example, an inlet of a pneumatic control pump can be connected with the pneumatic control connection interface 387E' and the outlet of the pneumatic control pump can be connected with the pneumatic control connection interface 387E". In such arrangement, operation of the pneumatic control pump in a first direction, for example, opens selector valve 360E' and closes selector valve 360E" thus connecting flow path 320E with the source of use composition connected at inlet connector 321E' (i.e. the measurement cycle is active). When the pneumatic control pump is activated in the second direction, selector valve 360E' is closed and selector valve 360E" is opened. This connects flow path 320E with the source of blank (e.g. water) connected at inlet connector 321E" (i.e. the reagent blank cycle is active). Thus, two pneumatic control pumps are required to control the laminate pump assembly 300F (i.e. one to control each of the flow paths via the control manifolds 371F, 372F, 373F, and one to control the selector valves 360E', 360E").

In addition, the embodiment of the laminate pump assembly 300 of FIG. 3A can be adapted for use as a peracid/peroxide concentration monitor. For example, connections for the peracid/peroxide concentration monitor can be as follows: a source of use composition can be connected with inlet connector 321A; a source of blank can be connected with inlet connector 321B; a source of reagent can be connected with inlet connector 320C; and a source of acid can be connected with inlet connector 321D. Thus, the dispersion of use composition and blank can be separately controlled, and the dispersion of reagent and acid can be simultaneously controlled. Such operation would require the use of three pneumatic control pumps (i.e. one each for flow paths 320A and 320B, and a third for flow paths 320C and 320D).

When assembled, the connection inlets of each laminate pump assembly embodiment described above (i.e. the laminate pump assembly 300 of FIG. 3A, and the laminate pump assembly 300F of FIG. 3F) can resemble the laminate pump assembly 200 of FIG. 2. That is, when assembled, the laminate pump assembly 200 can include connection inlets 220, 222 on its top surface 202 and control interfaces on its bottom surface 204 to facilitate easy connection of fluid sources.

Referring back to FIG. 1, one or more pneumatic control pumps 130 can be connected with the laminate pump assembly 110 to pneumatically control the pump cycle. Accordingly, the pneumatic control pumps utilized should be capable of delivering pneumatic fluid to and removing pneumatic fluid from the laminate pump assembly 110. Preferably, the pneumatic control fluid comprises air, however other pneumatic control fluids can be utilized. In some embodiments, for example, the pneumatic control pumps 130 can comprise reversible peristaltic pumps, such as a peristaltic micro pump SP100, model SP100VO with 12 V DC-20 RPM available from APT Instruments of Rochester, Ill., USA, or an ultra small peristaltic pump, model RP-Q1 available from Takasago Electric, Inc. of Nagoya, Japan. In some embodiments, the pneumatic fluid used to control each valve comprises air, however other fluids may be utilized. Of course other models or types of pneumatic control pump can be used, such as, for example gear pumps or syringe pumps.

Figure 11:
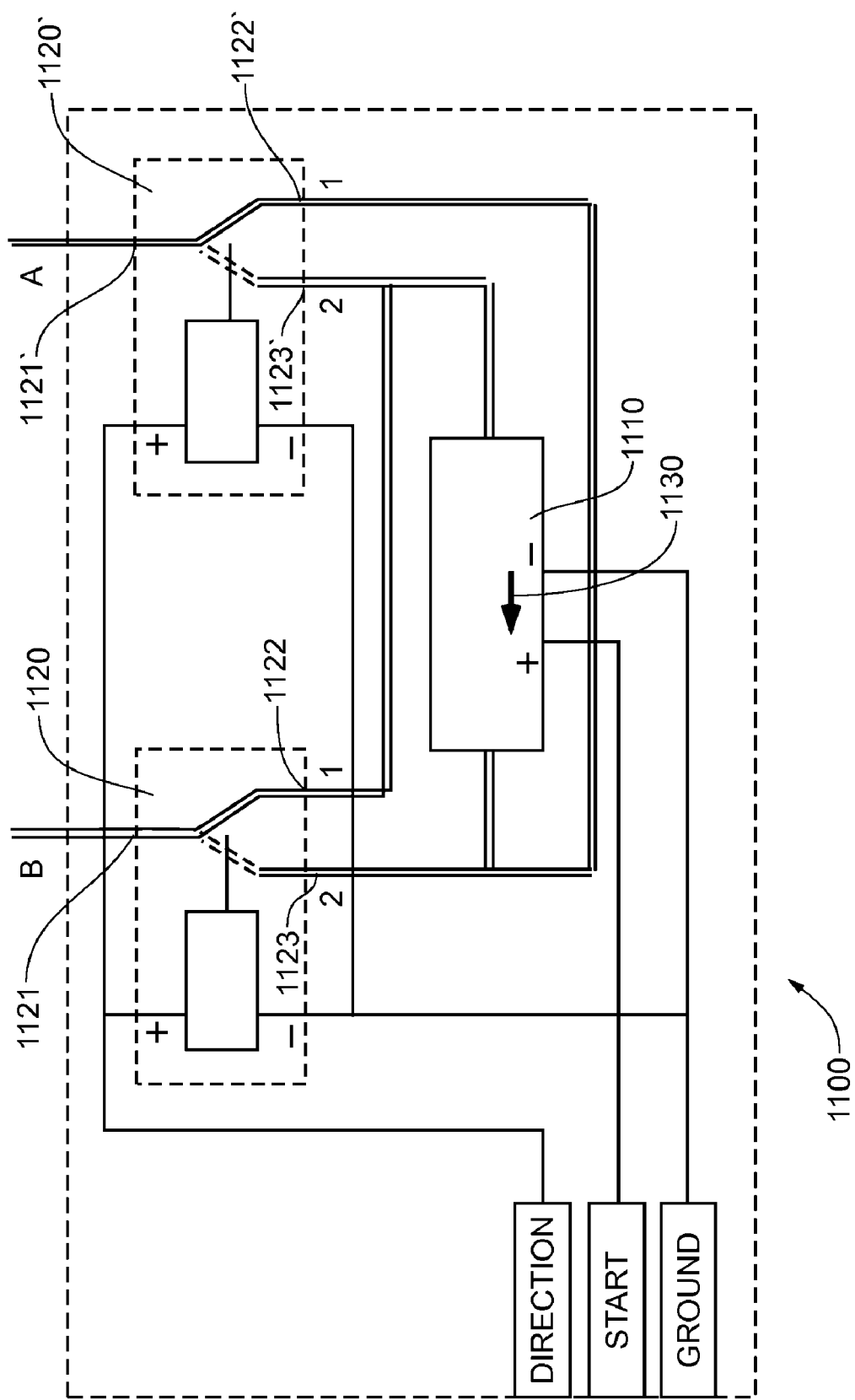
FIG. 11 is a schematic view of a reversible pneumatic control pump according to some embodiments.

Another example of a reversible pneumatic control pump 1100 is shown in FIG. 11. In this embodiment, the control pump 1100 comprises a uni-directional pump 1110 and a pair of three-way electrically actuated control valves 1120. The pneumatic connectors A, B are each connected with an outlet 1121 of one of the electronic control valves 1120. Inlets 1122, 1123 to each of the electronic control valves 1120 are connected with a network of tubing that allows for the direction of operation (i.e., pumping from pneumatic connector A to pneumatic connector B, or vice versa) of control pump 1100 to be controlled. For example, the uni-directional pump 1110 can comprise mini diaphragm pump VMP1624MM-12-60-CH available from Virtual Industries, Inc., Colorado Springs, Colo., US and the control valves 1120 can comprise, for example, sub-miniature valve model 161TO31 available from NResearch, Inc., West Caldwell, N.J., US.

In operation, the pump 1110 turns ON when a voltage (e.g. 12 Volts) is applied to the contacts Ground and Start. When the pump 1110 is on, it operates in a single direction, e.g. along arrow 1130. If no voltage is applied to the contact Direction both control valves 1120 are held in position 1. In this position, the network of tubing is connected such that the pump 1110 is pumping pneumatic fluid from pneumatic connector B to pneumatic connector A. Thus, pneumatic connector A is an output for high pressure and low pressure is provided at pneumatic connector B. When a voltage (e.g. 12 Volts) is applied to the contact Direction, both control valves 1120 switch to position 2. In this position, and without switching the direction of operation of pump 1110, the network of tubing is connected such that the direction of pneumatic fluid flow is reversed. Accordingly, pneumatic fluid is pumped from pneumatic connector A to pneumatic connector B. Thus, pneumatic connector B is an output for high pressure and the pressure at pneumatic connector A is lowered.

In a simple arrangement, the pneumatic control chamber 402' of each valve of each flow path can be connected with a dedicated, and separately controllable pneumatic control pump. However, in many embodiments, multiple pneumatic control chambers 402' are connected via a control manifold such that a single pneumatic control pump 130 can simultaneously control multiple valves. Accordingly, fewer pneumatic control pumps need be utilized. In addition, some pneumatic control pumps (e.g. the peristaltic pumps described above) operate as displacement pumps. Displacement pumps operate by displacing pneumatic fluid from a pump inlet to a pump outlet. Reversing the direction of pump operation, causes pneumatic fluid to be displaced from the pump outlet and delivered to the pump inlet. Accordingly, further efficiencies can be realized by selectively coupling the pump inlet and pump outlet of a reversible, displacement pump with specific pneumatic control chambers.

Figure 6:
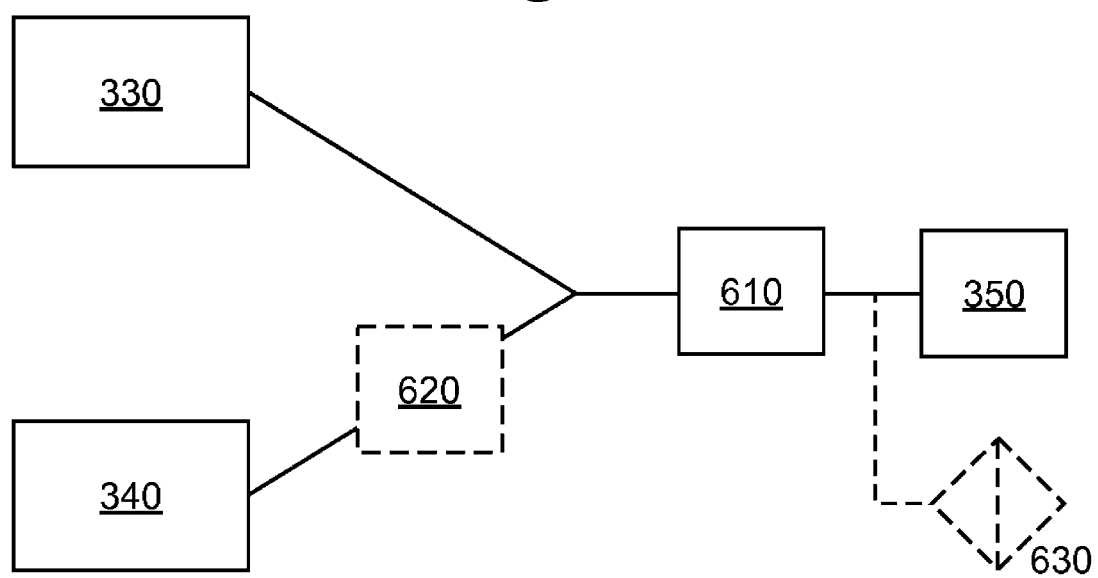
FIG. 6 is a schematic illustrating a pneumatic control pump connection scheme according to some embodiments.

FIG. 6 shows a schematic of how a single reversible, displacement control pump 610 can be connected with the valves of a single flow path, such as that shown in FIG. 3C. The reversible displacement control pump 610 can comprise any of the pneumatic control pumps discussed above, for example, a peristaltic pump or a control pump such as that shown in FIG. 11. In such an arrangement, the inlet of control pump 610 can be connected with the pneumatic control chamber 402' of the inlet valve 330, and the pneumatic control chamber 402' of the pump valve 340. Such connection can be facilitated by connecting the control pump inlet to pneumatic control pump connectors 381, 383, which in turn connect to control manifolds 371, 373, respectively in FIG. 3D. The control pump outlet can be connected with the pneumatic control chamber 402' of the outlet valve 350. Such connection can be facilitated by connecting the control pump outlet to pneumatic control pump connector 382, which in turn connects to control manifold 372. Accordingly, a single displacement control pump, can be utilized to control a single flow path, or indeed, all flow paths connected by control manifold. For example, with respect to FIG. 3A, two pneumatic control pumps can be utilized to control all four flow paths 320.

The connections shown in the schematic of FIG. 6 provide for operation of the flow path according to the above-described pump cycle 500. For example, as control pump 610 is actuated in the forward direction, pneumatic fluid is displaced from the inlet valve 330 and the pump valve 340. Thus, the inlet valve 330 and pump valve 340 open (502), (503). Optionally, a delay volume 620 can be provided between the pump valve 340 and the control pump 610 to provide the optional delay (504) between the opening of the inlet valve 330 and the opening of the pump valve. This delay 620 can be provided, for example, by increasing the volume of pneumatic control passage 384 with respect to pneumatic control passage 385 as shown in FIG. 3D. Also, during forward pump operation, the displaced pneumatic fluid is delivered to outlet valve 350, ensuring that the outlet valve 350 remains closed (503). Optionally, a filter 630 can also be connected with the pump outlet to provide for leakage of excess pneumatic fluid.

When the control pump 610 is actuated in the reverse direction, pneumatic fluid is drawn from the outlet valve 350, thereby causing it to open (506). The displaced pneumatic fluid is delivered to the inlet valve 330 (505), and (possibly after the optional delay 620) the pump valve 340 (507). Thus, the inlet valve 320 is closed as the outlet valve 350 is opened. Additionally, the pump valve 340 is closed, forcing fluid out through the open outlet valve 350.

The pump cycle 500 can be governed by a computer controller 160. For example, in some embodiments, this controller can be the same as the controller which is used to control the sensor and other instrumentation or it may be a dedicated controller. Indeed, a single controller can be utilized to implement a measurement or other operation sequence which includes the sample preparation sequence or pump cycle described above.

Figure 12:
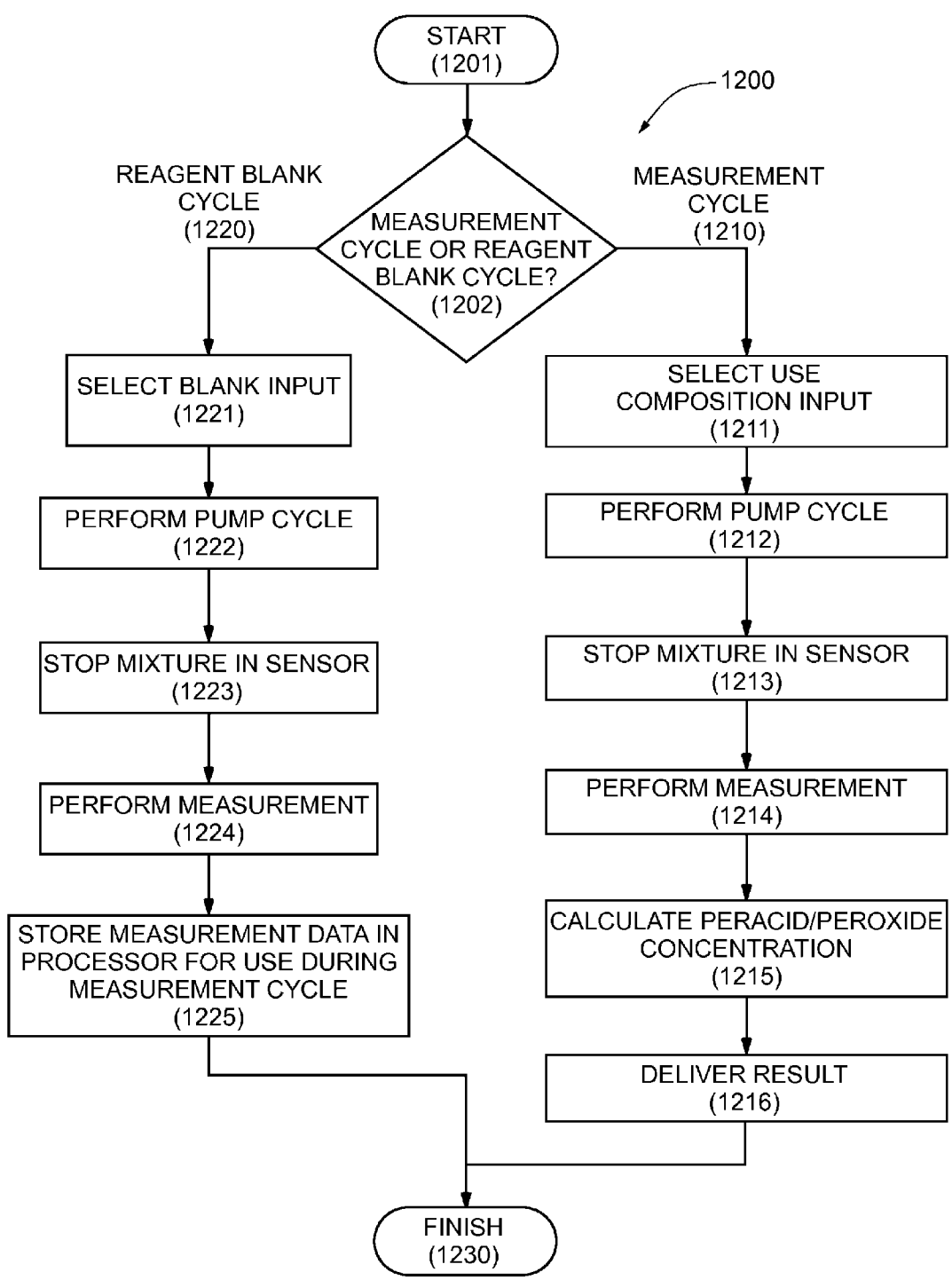
FIG. 12 is a flow chart illustrating an exemplary control operation for a peracid/peroxide concentration sensor according to some embodiments.

In some embodiments, the controller 160 can be adapted to implement multiple operation sequences. For example, FIG. 12 shows a flow chart of an exemplary control operation 1200 of a peracid/peroxide concentration sensor. This control operation 1200 will be described with reference to the laminate pump assembly 300F of FIG. 3F. The sequence begins (1201) with the system in an idle state. A user can then select which operation sequence to run (1202). In this embodiment, the control operation 1200 can provide two operation sequences: a measurement sequence (1210), and a reagent blank sequence (1220). The measurement sequence (1210) can be utilized to perform an actual measurement of the peracid/peroxide concentration of a volume of the use composition. The reagent blank sequence (1220) can be utilized to provide calibration data for the system which can be utilized during the measurement or other cycles.

In the measurement cycle (1210), the controller 160 manages the preparation and measurement of a sample mixture and the calculation of the mixtures properties. First, the use composition input (1211) is selected. For example, with respect to the laminate pump assembly 300F, this can be accomplished by actuating selector valves 360E', 360E" such that the selector valve connected with the source of use composition is opened, while the selector valve coupled with the source of blank is closed. A pump cycle can then be performed (1212). This can be accomplished, for example, by performing the pump cycle 500 shown in FIG. 5. In the embodiment of FIG. 3F, when the pump cycle 500 is performed with the use composition selector valve 360E' open, control manifolds 371F, 372F, 373F allow for the simultaneous delivery of use composition, reagent, and acid along flow paths 320E, 320F, 320G, respectively. Further, the pump cycle causes these volumes of fluid to be delivered via outlet channels 325 to integral mixer 390, where the fluids are mixed and delivered out of the laminate pump assembly 300F.

Once the pump cycle has been performed, the fluid mixture is stopped within the sensor (1213). While within the sensor, a measurement is performed (1214). In some embodiments, it can take approximately from 1 second to 15 seconds, e.g. 5 seconds, to perform the measurement and collect the necessary response data. The controller 160 can then calculate the peracid/peroxide concentration based upon the response data (1215). The resulting concentration information can then be delivered as the output of the system (1216). For example, the concentration can be utilized to control an alarm or the use composition usage in the case of a monitor. In the case of an analytical testing system, the determined concentration can be output, for example, to a display. At this point, the sequence operation is finished (1230) and the system can be returned to the starting state.

In the reagent blank cycle (1220), the controller 160 manages the preparation and measurement of a reagent blank. The controller then calculates calibration data based upon the reagent blank measurement data. In this operation, first the blank input is selected (1221). The blank can comprise water, for example. As above, the selection of the blank can be accomplished by actuation of one or more selector valves. Then, a pump cycle can be performed (1222). The pump cycle can be the same pump cycle 500 performed during the measurement cycle (1210), however the different connection provided to flow path 320E by the actuation of the selector valves, provides for a different mixture to be prepared. Once the mixture is prepared, it can be stopped within the sensor (1223) and a measurement can be performed (1224) just as was done in the measurement cycle (1210). Once the measurement has been performed, the obtained response data can be used to calculate calibration values which can be stored in controller or other system memory (1225). These calibration values can later be used by the controller during the calculation of the peracid/peroxide concentration (1215) during the measurement cycle (1210). At this point, the sequence operation is finished (1230) and the system can be returned to the starting state.

Of course, the sequence operation 1200 and cycles described herein with respect to FIG. 12 are but one exemplary embodiment of device operation according to the present invention. This specification should not be read to limit the devices or methods disclosed herein to such method as all others apparent to one of ordinary skill in the art should be considered within the scope of invention.

Referring back to FIG. 1, the microflow analytical system 100 includes instrumentation connected with the output channels of the laminate pump assembly 140, 150. In some embodiments, the instrumentation comprises a mixer 140 and a sensor 150. The mixer 140 can provide thorough mixing of metered fluid volumes dispensed by the laminate pump assembly 110. In a use composition monitor, appropriate mixing can ensure that the response data measured by the sensor 150 leads to an accurate determination of the characteristic of the use composition to be determined. The mixer 140 may be implemented using any conventional device designed to rapidly mix together two or more fluids. For example, the mixer 140 may be a piece of tubing with internal baffles that cause flow reversal of the fluids to result in rapid mixing. The mixer 140 may also be implemented using a knotted reactor, reaction coil, serpentine or other fluid mixing device known in the art. An example baffle-type static mixer is the Series 120 Individual Mixing Elements available from TAH Industries Inc, Robbinsville, N.J. However, it shall be understood that any suitable mixer may be used without departing from the scope of the present invention, and that the invention is not limited in this respect.

In addition, some embodiments include a mixer integral with the laminate pump assembly 110. For example, the laminate pump assembly 300 shown in FIGS. 3A and 3C includes an integral mixer 390. In this embodiment, the integral mixer 390 comprises a chamber formed within a layer 305 of the laminate pump assembly 300. The chamber includes connections to the outlet channels 325 of each of the flow paths 320. As fluid is simultaneously dispensed through the flow paths, it is injected into the mixer chamber 390. The simultaneous injection causes rapid mixing of the fluids before they are ejected from the mixer 390 along mixer outlet 391.

Mixed, or otherwise dispensed fluid can then be delivered to a sensor 150. The sensor measures at least one characteristic of the fluid mixture indicative of the properties to be determined. The measurements obtained by detector 150 are referred to herein as "response data." For example, properties to be determined can be the concentrations of peracid and/or hydrogen peroxide in a use composition. Controller 160 determines the properties based on the response data. In some embodiments, the sensor 150 is an optical detector that measures the transmittance and/or the absorbance of the fluid mixture. In such embodiments, the response data may be the optical transmittance data or optical absorbance data of the sample as a function of time. In other embodiments, the sensor 150 may measure other characteristics indicative of the particular property to be determined, such as fluorescence, pH, oxidation-reduction potential, conductivity, mass spectra and/or combinations thereof. In such embodiments, the response data would be the corresponding measured characteristic at the appropriate points in time. Example sensors 150 include photometric, pH, ORP, conductivity or other sensors. The photometric sensors utilized can operate in the visible, ultraviolet or infrared wavelength range, although other luminescence detection techniques may also be used without departing from the scope of the present invention. One example of a suitable commercially available photometric detector can be assembled using a DT-MINI-2 Deuterium Tungsten Source, FIA-Z-SMA-PEEK Flow Cell and USB4000 Miniature Fiber Optic Spectrometer, all available from Ocean Optics Inc., Dunedin, Fla. It shall be understood, however, that any suitable optical detector may be used without departing from the scope of the present invention, and that the invention is not limited in this respect. Indeed, an appropriate optical sensor may be any of those described for use with respect to U.S. patent application Ser. No. 12/370,369 filed Feb. 12, 2009, which is presently co-owned and is herein incorporated by reference.

Figure 7:
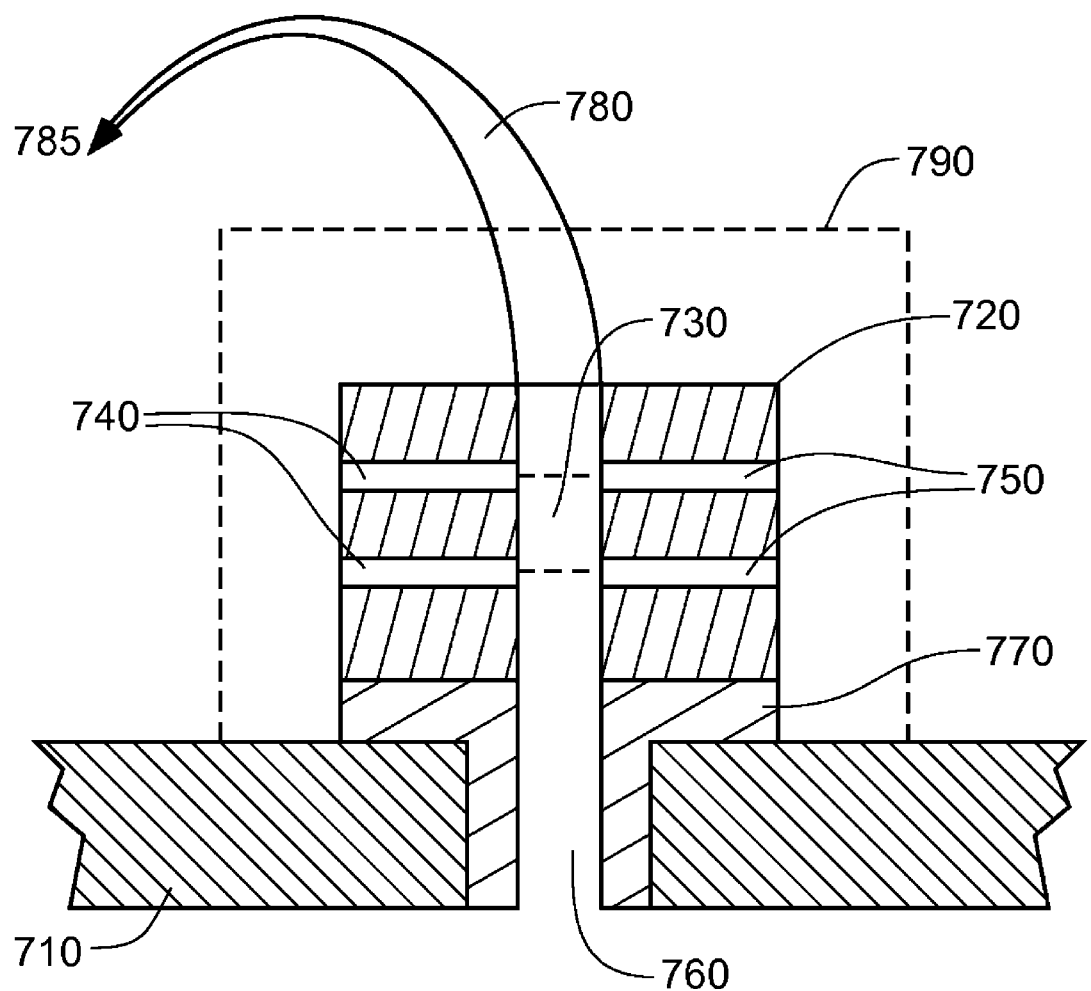
FIG. 7 is a cross-sectional view of a laminate pump assembly having an optical sensor coupled directly thereto according to some embodiments.

An optical sensor 150 may be coupled with the laminate pump assembly 110 via a length of tubing, or otherwise. For example, the cross-sectional view of FIG. 7 shows a portion of a laminate pump assembly 710 having an optical sensor 720 coupled directly thereto. The optical sensor 720 includes a flow channel 730 passing through the sensor body. Two emitter/detector pairs abut the flow channel 730. The emitter 740 of each pair emits light of a particular wavelength which is detected by a corresponding detector 750. In this embodiment, the laminate pump assembly 710 includes an integral mixer. The integral mixer delivers mixed fluid along a mixer outlet 760 which has a thermocouple insert 770 installed therein. An outlet tube 780 coupled with the sensor 720 delivers the measured fluid mixture to waste 785. The thermocouple insert 770 thermally links the optical sensor 720 (which is in direct contact with the thermocouple insert 770) with the mixer outlet 760 such that fluid passing through the mixer outlet is thermally adjusted based upon the temperature of the sensor 720. Such an arrangement allows for stabilization of fluid temperature and reduced variance in sensor performance. Some embodiments optionally include a temperature controlled environment 790 surrounding the sensor 720. The temperature controlled environment can comprise, for example, those as described in U.S. patent application Ser. No. 12/370,348 filed Feb. 12, 2009, which is presently co-owned and is herein incorporated by reference.

Figure 8:
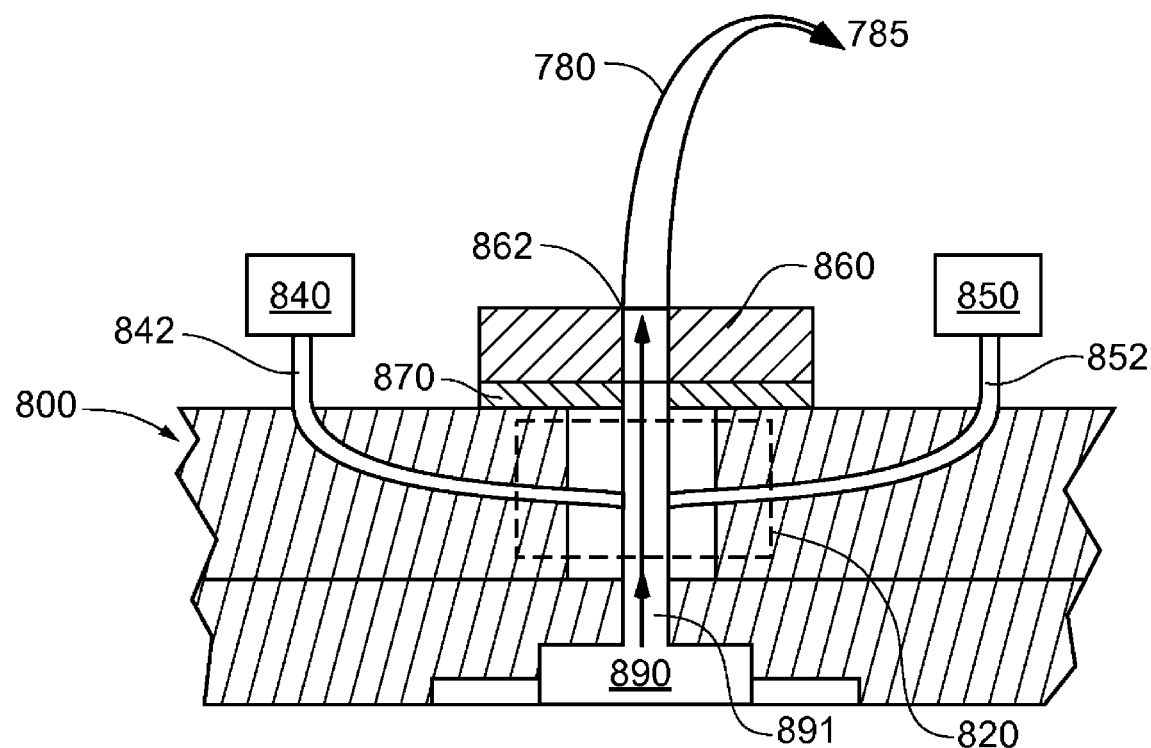
FIG. 8 is a cross-sectional view of a laminate pump assembly having an incorporated sensor according to some embodiments.

FIG. 8, shows yet another embodiment, where the sensor 820 has been incorporated into the laminate pump assembly 800. In this embodiment, a thermocouple insert 870 having opposing ports for receiving optical fibers 842, 852 is installed within the outlet channel 891 from an integral mixer 890 of the laminate pump assembly 800. An emitter 840 coupled with one of the optical fibers 842 and a detector 850 coupled with the other optical fiber 852 provide the sensor functionality. In this embodiment, a thermoelectric device 860 including a central port 862 has been coupled with the thermocouple 870. The thermoelectric device 860 can comprise, for example, a Peltier device which can provide for heating and/or cooling of the thermocouple insert 870. The thermocouple insert 870 can thus be utilized to regulate the temperature within the sensor.

An advantage of systems according to some embodiments of the present invention is that temperature stabilization can be facilitated easier than in other embodiments. This is because laminate pump assemblies according to embodiments of the invention enable the delivery of small quantities of fluids (e.g. less than 100 microliters). These smaller volumes of fluid can be temperature adjusted significantly more rapidly than larger volumes of fluid.

In the case of an optical sensor, the voltage response of the sensor corresponds to the amount of the light transmitted through the sample mixture. The sensor thus essentially measures the change of the sample solution optical properties within the sensor as a function of time. The transmittance is the ratio of the intensity of light coming out of the sample (I) to intensity of light incident to the sample ($I_0$), $T=I/I_0$. Once the transmittance of the sample is measured, the absorbance (A) of the sample may be calculated. The absorbance or optical density (A) is a logarithmic function of the transmittance; $A=-\log_{10}T=-\log_{10}I/I_0=\log_{10}I_0/I$. With respect to embodiments used to determine the concentrations of peracid and peroxide within a use composition, as is discussed in further detail below, the initial absorbance of the sample ($A_0$) is indicative of the concentration of peracid in the use composition and the sample absorbance variation over time is indicative of the concentration of hydrogen peroxide in the use composition. However, as is further indicated, this relationship may not hold true across wide ranging use composition concentrations. For example, at higher concentrations, e.g. above 500 ppm peracid, concentration of peracid is a function of both initial absorbance and, to a lesser degree, absorbance over time. Accordingly, to provide instruments capable of accommodating use with a wide concentration range, i.e. a range encompassing both concentration ranges described above, alternative methods must be utilized.

Additionally, the wavelength tested by the optical sensor can be selected based upon the particular application of the microflow analytical system. Indeed, some embodiments include sensors incorporating emitters of multiple wavelengths. With respect to peracid/peroxide concentration determination, wavelength selection is based on the spectral response of the triiodide complex, and may be within the range of 350 to 450 nanometers, for example. A two wavelength system may utilize the wavelengths 375 nanometers and 405 nanometers, for example.

As indicated above, some embodiments of microflow analytical systems are optimized for use as an on site use composition monitor. That is, there is a need for accurate and reliable sensors to measure use composition properties e.g. peracid and peroxide concentrations, when ambient temperature can vary in wide range. Unstable temperature inside of a system has been found to contribute to random variations in concentration readings. Potential causes of such temperature instability include environmental temperature variances and locally generated heat and air flow from components of the measurement system such as pumps, step motors, and electronic components, such as, the controller. Thus, some embodiments include additional features to adjust the temperature of the fluid mixture within the sensor or prior to reaching the sensor. In addition, systems according to some embodiments provide means for adjusting or stabilizing the temperature of sample prior to delivery to the detector to avoid the inconsistencies associated with in field operation.

Referring back to FIG. 1, the microflow analytical system 100 further comprises a plurality of sources of fluids. For example, in a peracid/peroxide concentration monitor, a connection to a source of use composition which contains a peracid and a peroxide as well as connections to reagent (e.g. potassium iodide) and an acid (e.g. acetic acid) are provided. Additionally, a source of water, for preparation of reagent blank may also be provided. In the case of a use composition monitor, the source of use composition can be connected to the laminate pump assembly by a length of tubing. Preferably, the length of tubing will be as short as possible, so that the monitor can draw from use composition representing fresh product currently being used. Other, components, e.g. reagents, acids, water, can be provided from a reservoir containing a volume of the fluid component. For example, in some embodiments, a bag reservoir containing the fluid component can be provided. The bag reservoir can include a puncturable interface which can be punctured by a needle connector input 220 (see e.g. FIG. 2). In any case, the connections to the fluid sources should be substantially air tight, so as to prevent air bubbles from entering the system. Air bubbles within the system can prevent the accurate metering of fluid through the flow paths. Fluid mixtures containing inaccurate volumes of the fluid components, can result in false positive measurement readings.

Figure 9A:
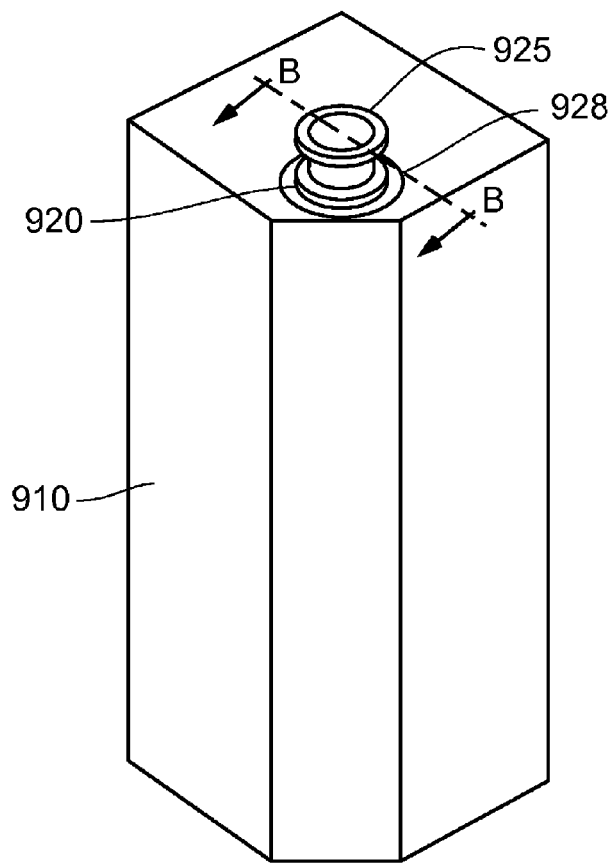
FIG. 9A is a perspective view of a disposable bag reservoir according to some embodiments.
Figure 9B:
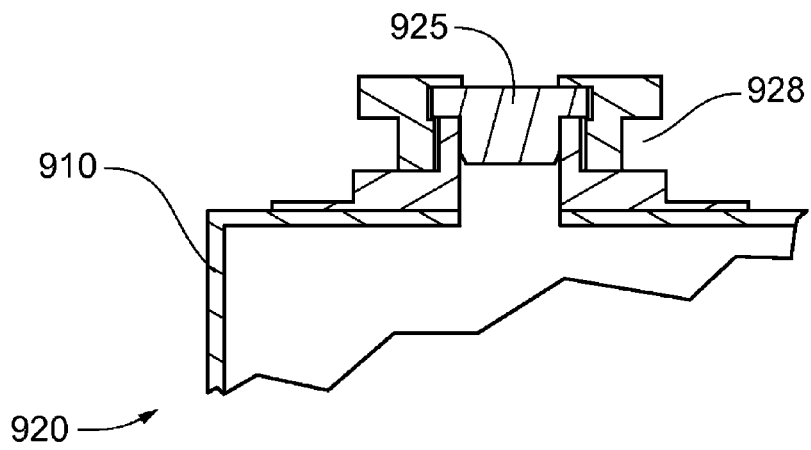
FIG. 9B is a partial cross-sectional view of the disposable bag reservoir of FIG. 9A taken along line B-B.

FIG. 9A shows an example of a disposable bag reservoir 900 according to some embodiments. The bag reservoir 900 comprises a sealed bag 910 adapted to hold a volume of the fluid. The sealed bag 910 can comprise a metalized plastic which can provide protection from ambient light. The bag reservoir 900 includes an extended neck portion 920 having a puncturable interface 925 which is hermetically sealed after the bag is filled with fluid. The extended neck portion 920 of the fluid bag 900 can include a groove 928 for locking the bag in place about the connection input or within a cartridge. FIG. 9B is a partial cross-sectional view of the extended neck portion 920 of the bag reservoir of FIG. 9A.

Figure 9C:
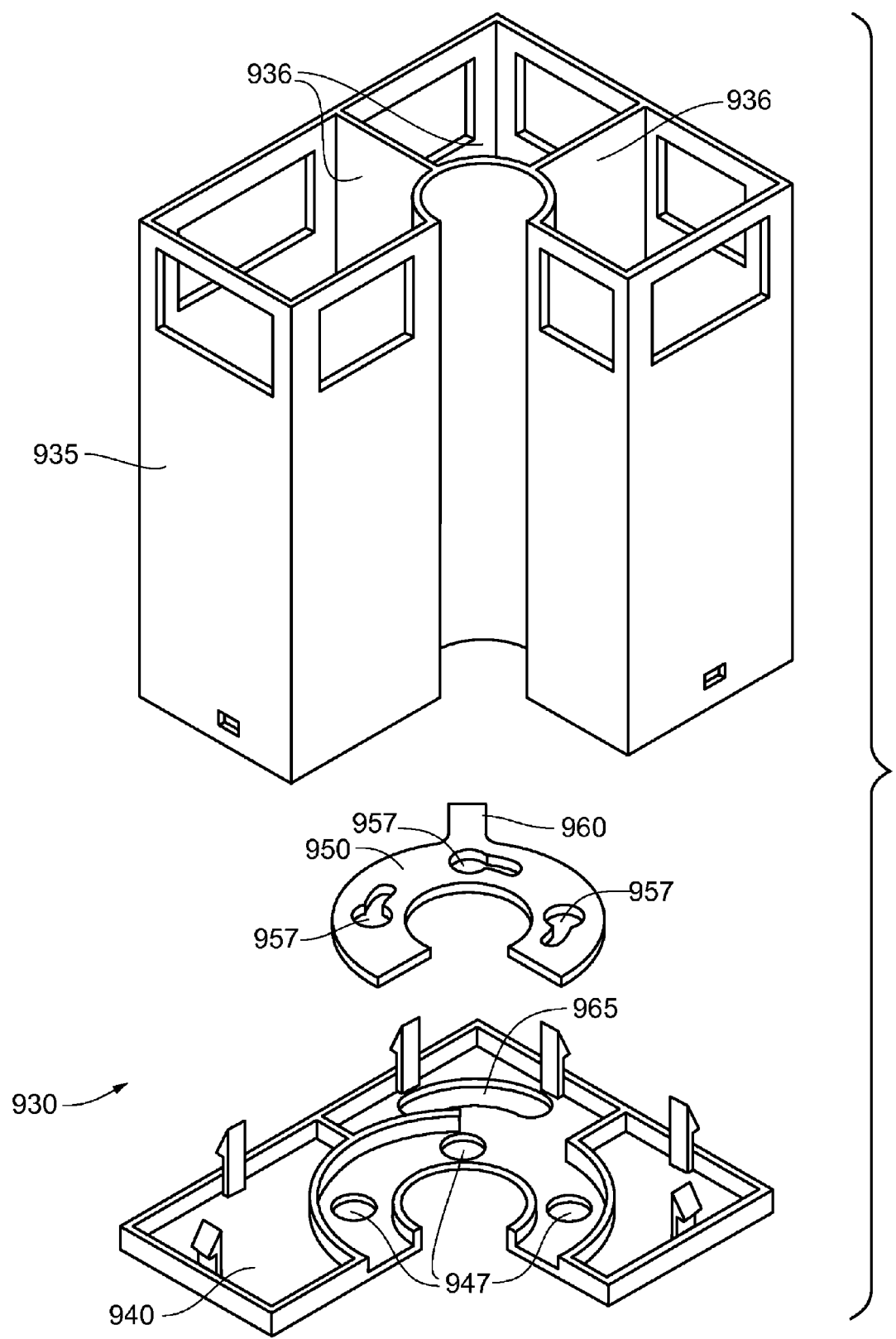
FIG. 9C is an exploded, top perspective view of a disposable bag reservoir cartridge according to some embodiments.
Figure 9D:
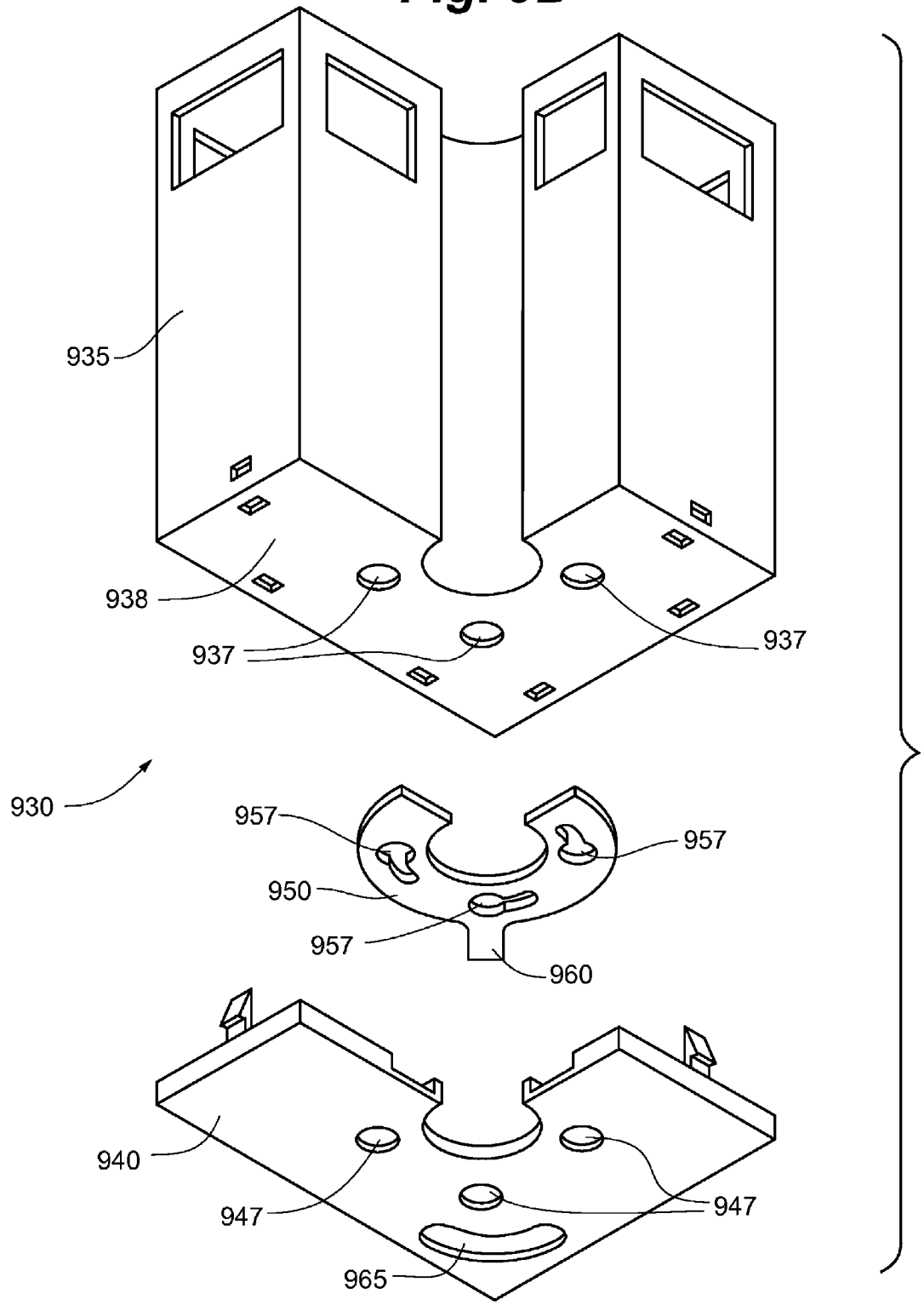
FIG. 9D is an exploded bottom perspective view of the disposable bag reservoir cartridge of FIG. 9C.

In some embodiments, the laminate pump assembly can be adapted to receive a cartridge comprising a fluid source for one or more of the fluids. An exemplary cartridge for three disposable bag reservoirs is shown in FIGS. 9C and 9D. The cartridge 930 comprises a rectangular shell 935 having a 90 degree cutout and three rectangular compartments 936. Each compartment 936 is adapted to receive a bag reservoir (e.g., the bag reservoir 900 of FIG. 9A) and includes an opening 937 in the bottom of the shell 938 to access the bag reservoirs. In some embodiments, the opening 937 can receive an extended neck portion 920 of the bag reservoir 900. The bottom part of the cartridge 930 can further comprise an attachment plate 940 and locking member 950 having openings 947, 957 that can be aligned with the openings 937 within the bottom of the shell 935. The lock member 950 can be received between the bottom of the shell 938 and the attachment plate 940 such that it can be rotated with limited range about a vertical axis. The lock member 950 has three openings 957 each with a round opening and an extension slit. In one rotational position, the round opening of each opening 957 of the lock member is between corresponding openings 937, 957 in the bottom of the shell 938 and the attachment plate 940. In such position, each fluid bag reservoir can be placed in corresponding compartments of the cartridge 936 with the extended neck portion turned down. The extended neck portion of each fluid bag extends through the openings in the bottom of the shell 937 and the attachment plate 947, and the opening in the lock member 957. The lock member can then be rotated to a second position, where the narrow slit is interlocked with the groove 928 on the neck 920 of the fluid bag reservoir 900. A tab 960 on the locking member 950 can protrude through a slot 965 within the attachment plate 940 to allow for such rotation. In such position all fluid bags are secured in the cartridge. In another embodiment, openings in each compartment of the cartridge 937 could have different shapes each corresponding to the shape of the extended neck portion of certain of the bag reservoirs to eliminate the possibility of mistake in the bag placement in the cartridge compartments.

Each of fluid bags shown on FIG. 9A has can contain approximately 200 ml of fluid. In some embodiments, such a volume can be sufficient for approximately 2000 analytical cycles. Once a bag reservoir has been emptied, (or after a predetermined number of measurement cycles, e.g. 2000) the cartridge can be removed from the laminate pump assembly and a bag reservoir or the entire cartridge can be replaced.

The use of a cartridge can make the fluid replacement operation easy and efficient. For example, in some embodiments, the laminate pump assembly can include guides such that the cartridge can be inserted in only a certain manner such that the puncturable interfaces of each bag are automatically aligned with the corresponding needle connector. Thus changing the fluid reservoirs can be as simple as inserting the cartridge and pressing down.

Referring back to FIG. 1, some embodiments further comprise a disposable waste bag connected with the waste line 170. The disposable waste bag can be placed under the laminate pump assembly to receive waste fluid once analysis has been performed. The disposable waste bag can further include a puncturable interface and can be secured under the laminate pump assembly with the extended neck portion oriented up. The bag interface should be punctured by a needle connector connected to the waste line 170 to maintain the airtight connection of the system. Embodiments including the three bag cartridge 930 shown in FIGS. 9C and 9D should include a disposable waste bag having a volume of at least approximately 850 ml. Initially the waste bag is empty. After 2000 analytical cycles it has approximately 800 ml of waste. The bag and waste can then be discarded and replaced with a new empty waste bag. This can be performed when the cartridge is refilled or replaced.

As used herein, the term "peracid" refers to any acid that in which the hydroxyl group (—OH) is replaced with the peroxy group (—OOH). The peracid(s) may be C2—C18 peracid(s), such as C2 (peracetic) acid and C8 (peroctanoic) acid. It shall be understood that the apparatus and/or methods of the present invention may detect the combined presence of all peracids in a sample, whether the sample contains one or more than one different peracids, and that the invention is not limited in this respect.

Peroxycarboxylic acids generally have the formula $R(CO_3H)_n$. In some embodiments, the R may be an alkyl, arylalkyl, cycloalkyl, aromatic or heterocyclic group, and n may be one or two.

Peroxycarboxylic acids useful in this invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof as well others known to those of skill in the art.

The concentrations of peracid and/or peroxide determined by use composition monitor may be used, for example, as feedback to controller to maintain the peracid concentration in the use composition within a predefined range and/or to cause the emptying of the use composition vessel and production of a new use composition when the hydrogen peroxide concentration exceeds the maximum peroxide threshold concentration. If, for example, the concentration of peracid in the use composition decreases below a predetermined level, the use composition may be replenished by adding a concentrated peracid composition to the use composition. As another example, if the concentration of peroxide in the use composition exceeds a predetermined level, the use composition may be replenished by emptying the use composition vessel of the spent use composition and generating a new use composition.

Use compositions including peracids and peroxides described herein may be used for a variety of domestic or industrial applications, e.g., to reduce microbial or viral populations on a surface or object or in a body or stream of water. The compositions may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or non-woven fabric, soft plastics and elastomers. The compositions may also be applied to soft surfaces such as food and skin (e.g., a hand). The use compositions may be employed as a foaming or non-foaming environmental sanitizer or disinfectant.

The compositions may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions may also be used in veterinary products such as mammalian skin treatments or in products for sanitizing or disinfecting animal enclosures, pens, watering stations, and veterinary treatment areas such as inspection tables and operation rooms. The compositions may be employed in an antimicrobial foot bath for livestock or people.

The compositions may be employed for reducing the population of pathogenic microorganisms, such as pathogens of humans, animals, and the like. The compositions may exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens may cause a varieties of diseases and disorders, including Mastitis or other mammalian milking diseases, tuberculosis, and the like. The compositions may reduce the population of microorganisms on skin or other external or mucosal surfaces of an animal. In addition, the compositions may kill pathogenic microorganisms that spread through transfer by water, air, or a surface substrate. The composition need only be applied to the skin, other external or mucosal surfaces of an animal water, air, or surface.

The compositions may also be used on foods and plant species to reduce surface microbial populations; used at manufacturing or processing sites handling such foods and plant species; or used to treat process waters around such sites. For example, the compositions may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions may be used to treat produce transport waters such as those found in flumes, pipe transports, cutters, slicers, blanchers, retort systems, washers, and the like. Particular foodstuffs that may be treated with compositions include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The composition may be useful in the cleaning or sanitizing of containers, processing facilities, or equipment in the food service or food processing industries. The compositions may be used on food packaging materials and equipment, including for cold or hot aseptic packaging. Examples of process facilities in which the compositions may be employed include a milk line dairy, a continuous brewing system, food processing lines such as pumpable food systems and beverage lines, etc. Food service wares may be disinfected with the compositions. For example, the compositions may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions may also be used on or in other industrial equipment and in other industrial process streams such as heaters, cooling towers, boilers, retort waters, rinse waters, aseptic packaging wash waters, and the like. The compositions may be used to treat microbes and odors in recreational waters such as in pools, spas, recreational flumes and water slides, fountains, and the like.

A filter containing a composition may reduce the population of microorganisms in air and liquids. Such a filter may remove water and air-born pathogens such as *Legionella*.

The compositions may be employed for reducing the population of microbes, fruit flies, or other insect larva on a drain or other surface.

The compositions may also be employed by dipping food processing equipment into the use solution, soaking the equipment for a time sufficient to sanitize the equipment, and wiping or draining excess solution off the equipment. The compositions may be further employed by spraying or wiping food processing surfaces with the use solution, keeping the surfaces wet for a time sufficient to sanitize the surfaces, and removing excess solution by wiping, draining vertically, vacuuming, etc.

The compositions may also be used in a method of sanitizing hard surfaces such as institutional type equipment, utensils, dishes, health care equipment or tools, and other hard surfaces. The composition may also be employed in sanitizing clothing items or fabrics which have become contaminated. The composition is contacted with any contaminated surfaces or items at use temperatures in the range of about 4° C. to 60° C., for a period of time effective to sanitize, disinfect, or sterilize the surface or item. For example, the composition may be injected into the wash or rinse water of a laundry machine and contacted with contaminated fabric for a time sufficient to sanitize the fabric. Excess composition may be removed by rinsing or centrifuging the fabric.

The compositions may be applied to microbes or to soiled or cleaned surfaces using a variety of methods. These methods may operate on an object, surface, in a body or stream of water or a gas, or the like, by contacting the object, surface, body, or stream with a composition. Contacting may include any of numerous methods for applying a composition, such as spraying the composition, immersing the object in the composition, foam or gel treating the object with the composition, or a combination thereof.

The composition may be employed for bleaching pulp. The compositions may be employed for waste treatment. Such a composition may include added bleaching agent.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

The peracid/peroxide use composition monitors described above determine the concentrations of peracid and/or hydrogen peroxide in the use composition using a kinetic assay procedure. This is accomplished by exploiting the difference in reaction rates between peracid and hydrogen peroxide when using, for example, a buffered iodide reagent to differentiate peracid and hydrogen peroxide concentrations when both these analyte compounds are present in the use composition. The use composition monitor may also determine the concentrations of peracid and/or hydrogen peroxide in the presence of other additional ingredients, such as acidulants, one or more stabilizing agents, nonionic surfactants, semipolar nonionic surfactants, anionic surfactants, amphoteric or ampholytic surfactants, adjuvants, solvents, additional antimicrobial agents or other ingredients which may be present in the use composition.

In a use composition including hydrogen peroxide and a peracid such as peroxyacetic acid, a buffered iodide changes color as it is oxidized by both the peroxyacetic acid and the hydrogen peroxide to form triiodide ion. However, as the peroxyacetic acid and the hydrogen peroxide in the use composition compete for the available iodide ions, reaction with the peroxyacetic acid proceeds at a faster rate than the reaction with the hydrogen peroxide, as shown in the following equations:

$$2CH_3COOOH + (excess)I^- \rightarrow I_3^- + 2CH_3COOH \text{ FASTER}$$

$$H_2O_2 + (excess)I^- + 2H^+ \rightarrow I_3^{31} + 2 H_2O \text{ SLOWER}$$

This difference in reaction rates may be exploited to differentiate peracid and hydrogen peroxide concentrations when both these analyte compounds are present in the use composition. An example reaction is described below and the results illustrated in FIGS. 3A-3D. It shall be understood, however, that the example below is for illustrative purposes only and that the invention is not limited to the particular reaction chemistry described in the example below, and that the invention is not limited in this respect.

Thus, embodiments of the microflow analytical system are disclosed. Although the present invention has been described in considerable detail with reference to certain disclosed embodiments, in particular a use composition monitor the concentrations of a peracid and peroxide within a use composition, the disclosed embodiments are presented for purposes of illustration and not limitation and other embodiments of the invention are possible. For example, microflow analytical systems as disclosed herein, can be readily adapted for use in other analytical applications. One skilled in the art will appreciate that various changes, adaptations, and modifications may be made without departing from the spirit of the invention and the scope of the appended claims.

What is claimed is:

1. A laminate pump assembly comprising:
a plurality of layers that define an inlet valve, a pump valve, an outlet valve, and a flow path extending through the inlet valve, the pump valve and the outlet valve, wherein the inlet valve, the pump valve and the outlet valve each comprise a chamber formed at the interface of two layers of the plurality of layers and a membrane dividing the chamber so as to define a fluid flow chamber and a control chamber, the control chamber being configured to expand in response to a control fluid entering the control chamber and collapse in response to the control fluid exiting the control chamber;
an inlet connector; and
an outlet channel,
wherein the inlet valve is connected to selectively provide fluid communication between the inlet connector and the pump valve, and the outlet valve is connected to selectively provide fluid communication between the pump valve and the outlet channel.

2. The laminate pump assembly of claim 1, further comprising a mixer connected downstream of the outlet valve.

3. The laminate pump assembly of claim 2, wherein the mixer comprises a mixing chamber formed within at least one layer of the plurality of layers.

4. The laminate pump assembly of claim 1, further comprising an optical sensor configured to measure an optical characteristic of a fluid flowing through the flow path.

5. The laminate pump assembly of claim 4, wherein at least a portion of the optical sensor is incorporated into at least one of the layers of the plurality of layers.

6. The laminate pump assembly of claim 1, wherein the plurality of layers comprise a substantially rigid material.

7. The laminate pump assembly of claim 6, wherein the membrane comprises a fluoropolymer.

8. The laminate pump assembly of claim 1, further comprising a pneumatic control pump configured to inject a pneumatic control fluid into the control chamber so as to expand the control chamber and thereby close the fluid flow chamber.

9. The laminate pump assembly of claim 8, wherein the pneumatic control pump is further configured to withdraw the pneumatic control fluid from the control chamber so as to collapse the control chamber and thereby open the fluid flow chamber.

10. The laminate pump assembly of claim 1, wherein the chamber of the inlet valve, the chamber of the pump valve, and the chamber of the outlet valve are each formed at the interface of the same two layers of the plurality of layers.

11. A method comprising:
introducing a fluid into a flow path of a laminate pump assembly, wherein the laminate pump assembly comprises a plurality of layers that define an inlet valve, a pump valve, an outlet valve, and the flow path, and wherein the inlet valve, the pump valve and the outlet valve each comprise a chamber formed at the interface of two layers of the plurality of layers and a membrane dividing the chamber so as to define a fluid flow chamber and a control chamber;
introducing a control fluid into the control chamber of at least one of the inlet valve, the pump valve and outlet valve so as to expand the control chamber and close the fluid flow chamber; and
withdrawing the control fluid from the control chamber of the at least one of the inlet valve, the pump valve and outlet valve so as to collapse the control chamber and open the fluid flow chamber,
wherein the inlet valve is connected to selectively provide fluid communication between an inlet connector and the pump valve, and the outlet valve is connected to selectively provide fluid communication between the pump valve and an outlet channel.

12. The method of claim 11, wherein the fluid comprises a use composition that includes a peracid and a peroxide.

13. The method of claim 11, further comprising mixing the fluid downstream of the outlet valve.

14. The method of claim 13, wherein mixing the fluid comprises passing the fluid through a mixing chamber formed within at least one layer of the plurality of layers.

15. The method of claim 11, further comprising measuring an optical characteristic of a fluid flowing through the flow path.

16. The method of claim 15, wherein measuring the optical characteristic comprises measuring the optical characteristic via an optical sensor at least partially incorporated into a layer of the plurality of layers.

17. The method of claim 11, wherein the plurality of layers comprise a substantially rigid material.

18. The method of claim 11, wherein the membrane comprises a fluoropolymer.

19. The method of claim 11, wherein introducing the control fluid into the control chamber comprises activating a pneumatic control pump so as to introduce a pneumatic control fluid into the control chamber.

20. The method of claim 19, wherein withdrawing the control fluid from the control chamber comprises activating the pneumatic control pump so as to withdraw the control fluid from the control chamber.

* * * * *